(12) United States Patent
Kulshrestha et al.

(10) Patent No.: US 11,324,861 B2
(45) Date of Patent: May 10, 2022

(54) RECYCLED RESIN COMPOSITIONS AND DISPOSABLE MEDICAL DEVICES MADE THEREFROM

(71) Applicant: Becton, Dickinson and Company, Franklin Lakes, NJ (US)

(72) Inventors: Ankur S. Kulshrestha, Hillsborough, NJ (US); Yan Yevmenenko, New York, NY (US); Dinesh S. Kommireddy, Derry, NH (US); Andrew Wong, Morristown, NJ (US); Behzad Mottahed, Upper Montclair, NJ (US); Michael V. Quinn, East Hanover, NJ (US); Mildred Calistri-Yeh, Florham Park, NJ (US); Lourdes Pia L. Amora, Glenview, IL (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 591 days.

(21) Appl. No.: 14/868,289

(22) Filed: Sep. 28, 2015

(65) Prior Publication Data

US 2016/0015867 A1 Jan. 21, 2016

Related U.S. Application Data

(62) Division of application No. 13/289,226, filed on Nov. 4, 2011, now abandoned.

(51) Int. Cl.
*A61L 31/04* (2006.01)
*A61M 5/315* (2006.01)
(Continued)

(52) U.S. Cl.
CPC .......... *A61L 31/048* (2013.01); *A61L 31/143* (2013.01); *A61M 5/3129* (2013.01);
(Continued)

(58) Field of Classification Search
CPC .......... A61M 5/31511; A61M 5/31513; A61M 2005/31518; A61M 5/315; A61M 5/31501; A61M 5/31525; A61M 2005/31515
(Continued)

(56) References Cited

U.S. PATENT DOCUMENTS 5,075,057 A 12/1991 Hoedl
5,084,018 A 1/1992 Tsao
(Continued)

FOREIGN PATENT DOCUMENTS

CN 2915133 6/2007
CN 101035581 9/2007
(Continued)

OTHER PUBLICATIONS

Final Office Action in U.S. Appl. No. 13/289,226, dated Mar. 27, 2014, 9 pages.
(Continued)

*Primary Examiner* — Kevin C Sirmons
*Assistant Examiner* — Leah J Swanson
(74) *Attorney, Agent, or Firm* — Servilla Whitney LLC

(57) ABSTRACT

Syringe plunger rods comprising an elongate body formed from a composition comprising one or more of virgin material, a sterilization-stable recycled resin and a biobased compositions are described. Plunger rods comprising a plurality of ribs, some of which may have a plurality of openings, are also described. The plunger rods requiring less material while maintaining sufficient structural integrity to function properly.

2 Claims, 30 Drawing Sheets

(51) Int. Cl.
*A61M 5/31* (2006.01)
*A61L 31/14* (2006.01)
*A61B 17/00* (2006.01)
*A61B 17/3211* (2006.01)

(52) U.S. Cl.
CPC ............... *A61M 5/31511* (2013.01); *A61B 2017/00955* (2013.01); *A61B 2017/32113* (2013.01)

(58) Field of Classification Search
USPC .................................................. 604/227
See application file for complete search history.

(56) References Cited

U.S. PATENT DOCUMENTS

| | | | |
|---|---|---|---|
| 5,129,884 A | 7/1992 | Dysarz | |
| 5,215,524 A | 6/1993 | Vallelunga et al. | |
| 5,226,897 A | 7/1993 | Nevens | |
| 5,263,934 A * | 11/1993 | Haak | A61M 5/322 604/110 |
| 5,271,500 A | 12/1993 | Szacon | |
| 5,277,869 A | 1/1994 | Glazer et al. | |
| 5,328,484 A | 7/1994 | Somers et al. | |
| 5,350,562 A | 9/1994 | Anthony | |
| 5,395,681 A | 3/1995 | Hargarter et al. | |
| 5,423,757 A * | 6/1995 | Olovson | A61M 5/31511 604/110 |
| 5,427,737 A | 6/1995 | Glazer et al. | |
| 5,462,531 A * | 10/1995 | Novacek | A61L 2/28 604/110 |
| 5,462,794 A | 10/1995 | Lindemann et al. | |
| 5,508,004 A | 4/1996 | Held et al. | |
| 5,520,642 A | 5/1996 | Bigagli et al. | |
| 5,557,905 A | 9/1996 | Harding | |
| 5,558,280 A | 9/1996 | Morgan | |
| 5,582,793 A | 12/1996 | Glazer et al. | |
| 5,597,530 A | 1/1997 | Smith et al. | |
| 5,650,224 A * | 7/1997 | March | E02D 5/00 442/62 |
| 5,686,527 A | 11/1997 | Laurin et al. | |
| 5,693,026 A | 12/1997 | Spinello | |
| 5,693,278 A | 12/1997 | Clements | |
| 5,777,330 A * | 7/1998 | Murase | G01N 21/3563 250/339.13 |
| 5,785,260 A | 7/1998 | Morgan | |
| 5,824,745 A | 10/1998 | Brown | |
| 5,830,396 A | 11/1998 | Higgins et al. | |
| 5,833,669 A * | 11/1998 | Wyrick | A61M 5/31591 604/234 |
| D412,206 S | 7/1999 | Basile et al. | |
| 5,998,019 A | 12/1999 | Rosenbaum et al. | |
| 6,004,297 A | 12/1999 | Steenfeldt-Jensen et al. | |
| 6,053,314 A | 4/2000 | Pittman | |
| 6,142,978 A | 11/2000 | Niedospial, Jr. et al. | |
| 6,168,862 B1 | 1/2001 | Rosenbaum et al. | |
| 6,242,525 B1 | 6/2001 | Raetzsch | |
| 6,261,655 B1 | 7/2001 | Rosenbaum et al. | |
| 6,293,856 B1 | 9/2001 | Hertz et al. | |
| 6,297,322 B1 | 10/2001 | Ding et al. | |
| 6,348,272 B1 | 2/2002 | Haveaux | |
| 6,391,008 B1 | 5/2002 | Tsai | |
| 6,398,763 B1 * | 6/2002 | Richardson | B05C 17/00593 604/218 |
| 6,402,721 B1 | 6/2002 | Lo | |
| 6,416,323 B1 | 7/2002 | Grenfell et al. | |
| 6,478,780 B1 | 11/2002 | Shields | |
| 6,500,129 B1 | 12/2002 | Mahurkar | |
| 6,565,529 B1 | 5/2003 | Kimber et al. | |
| 6,712,207 B2 | 3/2004 | Panek, Jr. et al. | |
| 6,764,465 B2 | 7/2004 | Chen | |
| 6,792,662 B2 | 9/2004 | Samuel | |
| 6,808,820 B2 | 10/2004 | Lee et al. | |
| 6,878,131 B2 | 4/2005 | Novacek et al. | |
| 6,881,493 B2 | 4/2005 | Haveaux et al. | |
| 6,881,790 B1 | 4/2005 | Laurin | |
| 6,997,904 B2 | 2/2006 | Sculati | |
| 7,191,777 B2 | 3/2007 | Brand et al. | |
| 7,226,956 B2 | 6/2007 | Wilkes et al. | |
| 7,243,792 B2 | 7/2007 | Panek, Jr. et al. | |
| 7,387,615 B2 * | 6/2008 | Coelho | A61M 5/3216 604/110 |
| 7,393,590 B2 | 7/2008 | Scheer et al. | |
| 7,531,226 B2 | 5/2009 | Lee et al. | |
| 7,592,408 B2 | 9/2009 | Wilson, Jr. et al. | |
| 7,596,844 B2 | 10/2009 | Japunitch et al. | |
| 7,600,639 B2 | 10/2009 | Japuntich et al. | |
| 7,740,610 B2 | 6/2010 | Moh et al. | |
| 7,877,849 B2 | 2/2011 | Panek, Jr. et al. | |
| 8,002,754 B2 | 8/2011 | Kawamura et al. | |
| D667,107 S | 9/2012 | Mottahed | |
| D667,108 S | 9/2012 | Mottahed | |
| D667,109 S | 9/2012 | Mottahed | |
| D673,268 S | 12/2012 | Kommireddy | |
| D673,675 S | 1/2013 | Wong | |
| D713,028 S | 9/2014 | Yevmenenko | |
| 2001/0056259 A1 | 12/2001 | Skinkle et al. | |
| 2003/0038046 A1 | 2/2003 | Panek, Jr. et al. | |
| 2003/0040701 A1 | 2/2003 | Dalmose | |
| 2003/0213714 A1 | 11/2003 | Moats et al. | |
| 2004/0030345 A1 * | 2/2004 | Aurin | A61B 17/8822 606/92 |
| 2004/0099555 A1 | 5/2004 | Panek, Jr. et al. | |
| 2004/0148002 A1 * | 7/2004 | Cheng | A61L 31/10 623/1.11 |
| 2004/0235970 A1 | 11/2004 | Smith et al. | |
| 2004/0235983 A1 * | 11/2004 | Stadler | B27N 3/002 523/122 |
| 2005/0038185 A1 * | 2/2005 | Sullivan | C08L 27/06 525/63 |
| 2005/0121343 A1 | 6/2005 | Miller et al. | |
| 2005/0127579 A1 * | 6/2005 | Suzuki | B29B 17/0042 264/572 |
| 2005/0179153 A1 * | 8/2005 | Riise | B03C 7/00 264/40.1 |
| 2005/0192534 A1 | 9/2005 | Wolbring et al. | |
| 2005/0218142 A1 | 10/2005 | Finnestad et al. | |
| 2005/0228682 A1 | 10/2005 | Firestone, III | |
| 2006/0161106 A1 | 7/2006 | Wu | |
| 2006/0226247 A1 * | 10/2006 | Abramson | C08L 2666/02 238/1 |
| 2007/0016145 A1 | 1/2007 | Berler | |
| 2007/0068832 A1 | 3/2007 | Anderson et al. | |
| 2007/0068834 A1 | 3/2007 | Smudde et al. | |
| 2007/0069490 A1 | 3/2007 | Japuntich et al. | |
| 2007/0078402 A1 | 4/2007 | Yang | |
| 2007/0088291 A1 | 4/2007 | Weilbacher | |
| 2007/0299307 A1 | 12/2007 | Lew et al. | |
| 2008/0058736 A1 | 3/2008 | Reshamawala | |
| 2008/0065027 A1 | 3/2008 | Sharp | |
| 2008/0067093 A1 | 3/2008 | Japuntich et al. | |
| 2008/0067094 A1 | 3/2008 | Japuntich et al. | |
| 2008/0067100 A1 | 3/2008 | Japuntich et al. | |
| 2008/0073231 A1 | 3/2008 | Clayton et al. | |
| 2008/0073232 A1 | 3/2008 | Reshamwala et al. | |
| 2008/0073251 A1 | 3/2008 | Reshamwala et al. | |
| 2008/0076879 A1 | 3/2008 | Resemdes et al. | |
| 2008/0113887 A1 | 5/2008 | Scheer et al. | |
| 2008/0140032 A1 | 6/2008 | O'Malley | |
| 2008/0183140 A1 | 7/2008 | Paproski et al. | |
| 2008/0300550 A1 | 12/2008 | Schiller et al. | |
| 2009/0032423 A1 | 2/2009 | Japuntich | |
| 2009/0048560 A1 | 2/2009 | Caizza et al. | |
| 2009/0068412 A1 | 3/2009 | Nahmias et al. | |
| 2009/0076450 A1 | 3/2009 | Caizza et al. | |
| 2009/0111719 A1 | 4/2009 | Stoll et al. | |
| 2009/0120821 A1 | 5/2009 | Japuntich et al. | |
| 2009/0131869 A1 | 5/2009 | Caizza et al. | |
| 2009/0131878 A1 * | 5/2009 | Kawamura | A61M 5/31511 604/228 |
| 2009/0145901 A1 | 6/2009 | Finnestad et al. | |
| 2009/0230008 A1 | 9/2009 | Miller et al. | |
| 2010/0030159 A1 | 2/2010 | Li | |

(56) References Cited

U.S. PATENT DOCUMENTS

| | | | |
|---|---|---|---|
| 2010/0041937 A1 | 2/2010 | Gonzelez | |
| 2010/0062921 A1 | 3/2010 | Veiseh | |
| 2010/0104872 A1 | 4/2010 | Lu | |
| 2010/0155400 A1 | 6/2010 | Finnestad et al. | |
| 2010/0282623 A1 | 11/2010 | Reshamwala | |
| 2010/0286609 A1* | 11/2010 | Mahurkar | A61M 5/3234 604/110 |
| 2011/0068036 A1 | 3/2011 | Ji et al. | |
| 2011/0071230 A1 | 3/2011 | Ji | |
| 2012/0046411 A1 | 2/2012 | Kulshrestha et al. | |
| 2012/0071853 A1* | 3/2012 | Ingram | A61M 5/31511 604/500 |

FOREIGN PATENT DOCUMENTS

| | | |
|---|---|---|
| CN | 101743026 A | 6/2010 |
| DE | 4319989 | 12/1994 |
| DE | 19726105 | 12/1998 |
| EP | 0665327 | 8/1995 |
| EP | 1702637 | 9/2006 |
| EP | 2000164 | 12/2008 |
| JP | H04-051959 U | 5/1992 |
| JP | H06506615 A | 7/1994 |
| JP | 2002-059082 | 2/2002 |
| JP | 2004033509 A | 2/2004 |
| JP | 2009-286106 | 12/2009 |
| JP | 2010017938 A | 1/2010 |
| JP | 2011072670 A | 4/2011 |
| WO | WO-91/01396 | 2/1991 |
| WO | WO-00/54885 | 9/2000 |
| WO | WO-01/34230 | 5/2001 |
| WO | WO-2006/097105 | 9/2006 |
| WO | WO-2008/018920 | 2/2008 |
| WO | WO-2008/018921 | 2/2008 |
| WO | WO-2008/039438 | 4/2008 |
| WO | WO-2008/106759 | 9/2008 |
| WO | 2008151239 A2 | 12/2008 |
| WO | WO-2011/035119 | 3/2011 |
| WO | 2012024413 A1 | 2/2012 |

OTHER PUBLICATIONS

Final Office Action in U.S. Appl. No. 13/289,226, dated May 28, 2015, 8 pages.

Non-Final Office Action in U.S. Appl. No. 13/289,226, dated Apr. 26, 2013, 10 pages.

Non-Final Office Action in U.S. Appl. No. 13/289,226, dated Jan. 1, 2015, 8 pages.

PCT International Search Report in PCT/US2012/062208, dated Feb. 4, 2013, 3 pages.

PCT International Written Opinion in PCT/US2012/062208, dated Feb. 4, 2013, 5 pages.

PCT International Preliminary Report on Patentability in PCT/US2012/062208, dated May 15, 2014, 8 pages.

Zhao, Ruixiang, et al., Emerging Biodegradable Materials: starch- and protein-based bio-nanocomposites, *J Mater Sci* (2008) 43:3058-3071 Mar. 15, 2008, 14 pages.

Meran, Cemal et al, "Examination of the possibility of recycling and utilizing recycled polyethylene and polypropylene", Materials and Design 29, 2008, pp. 701-705.

Weaver, Laura B. et al, "Improving the Mechanical Properties of Polythylene and Polypropylene Recycled Streams using Polyefin Elastomers and Functionalized Polyolefins", ANTEC 2011, 2011, 15 pgs.

* cited by examiner

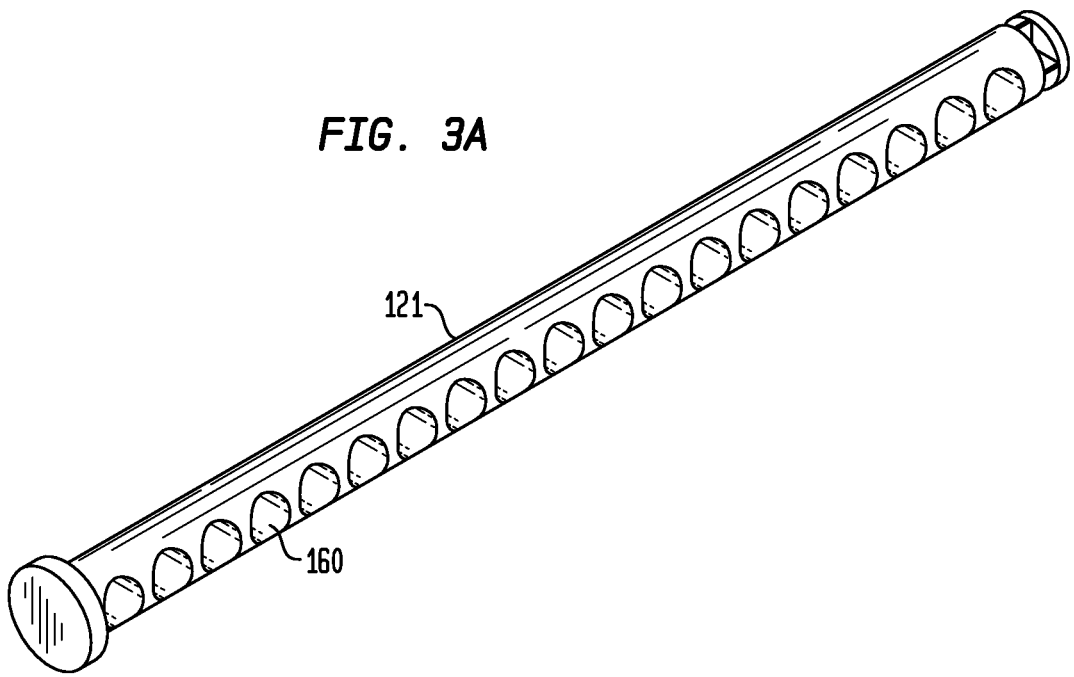
FIG. 3A
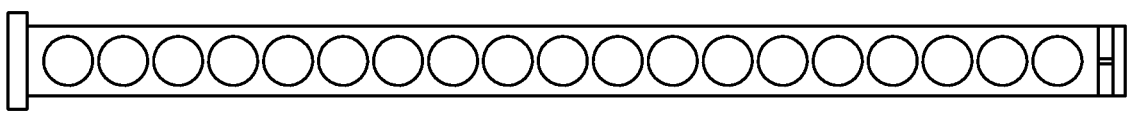
FIG. 3B
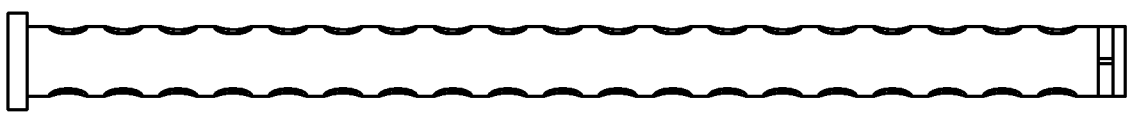
FIG. 3C
FIG. 3D
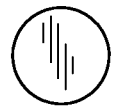
FIG. 3E

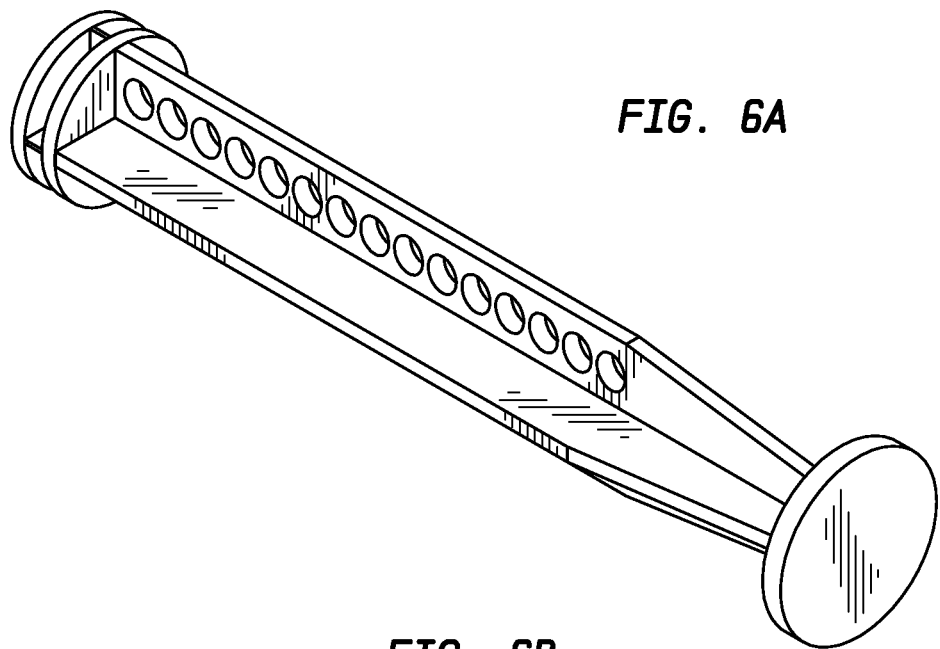
FIG. 6A
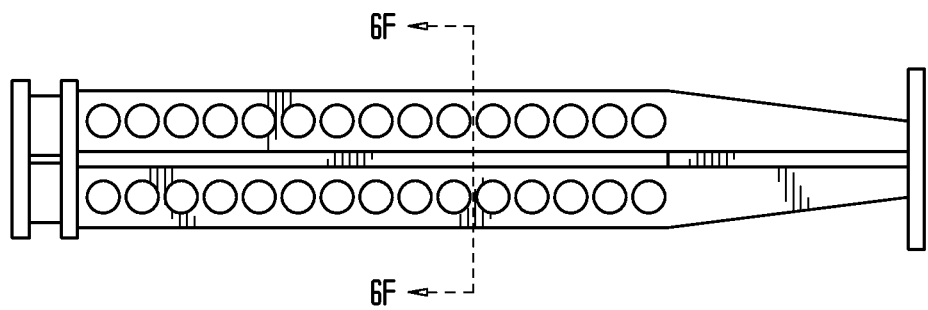
FIG. 6B
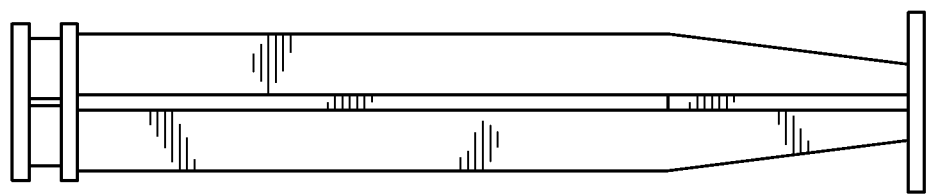
FIG. 6C
FIG. 6D
FIG. 6E
FIG. 6F
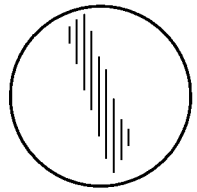
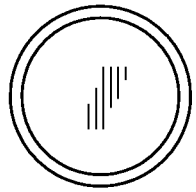
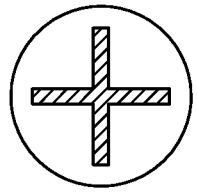

FIG. 8A
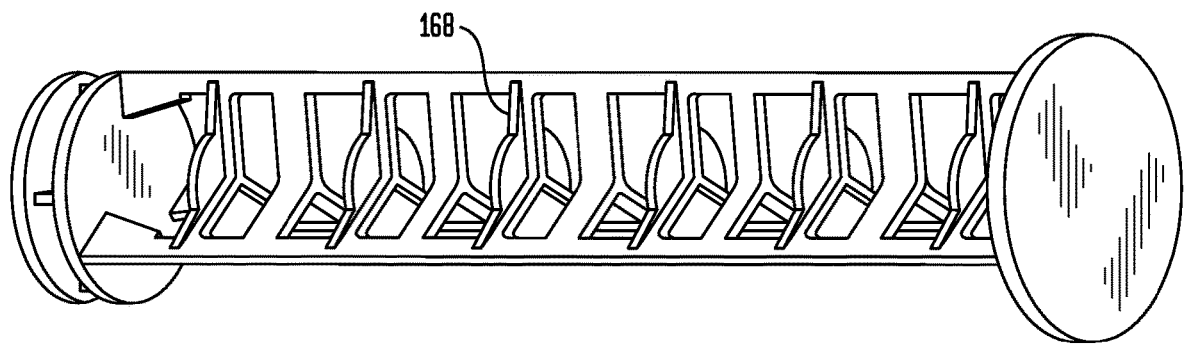
FIG. 8B
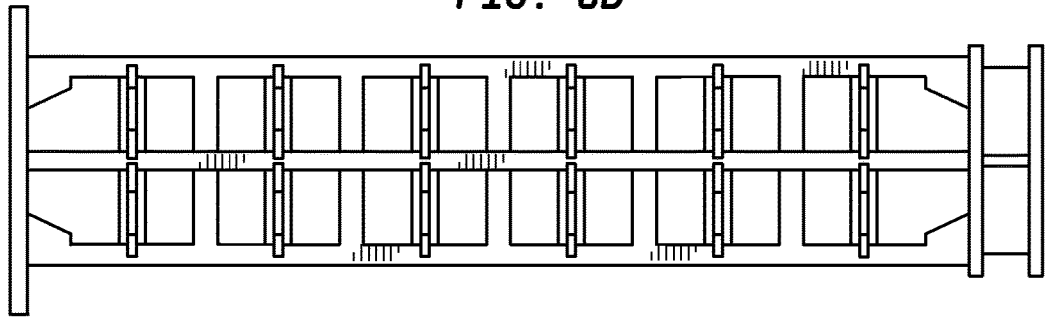
FIG. 8C
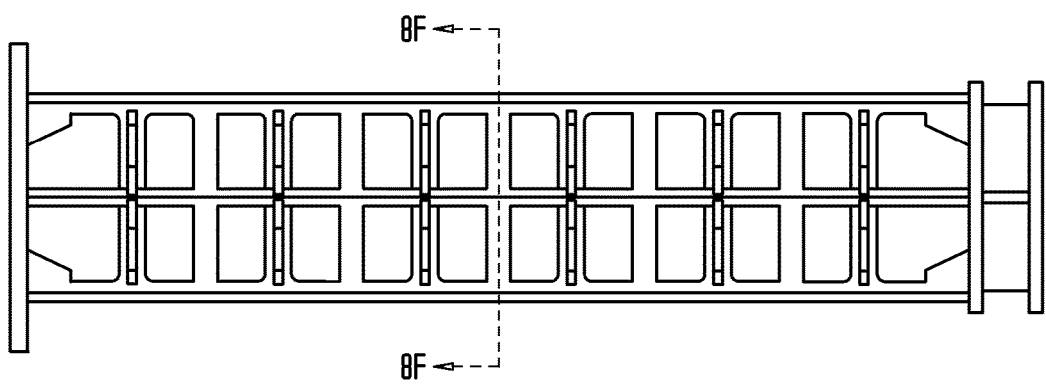
FIG. 8D         FIG. 8E         FIG. 8F
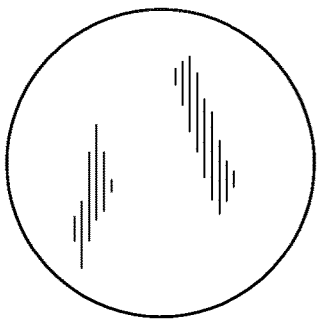 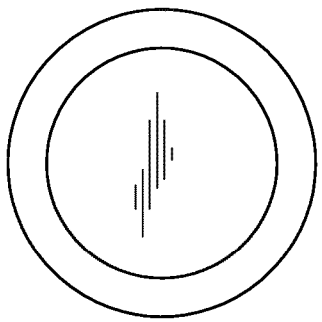 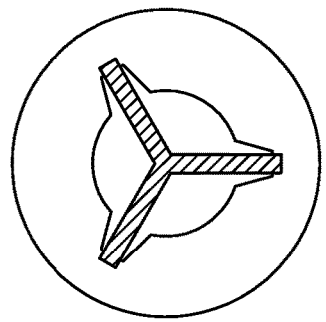

| FIG. 12D | FIG. 12E | FIG. 12F |

FIG. 13A
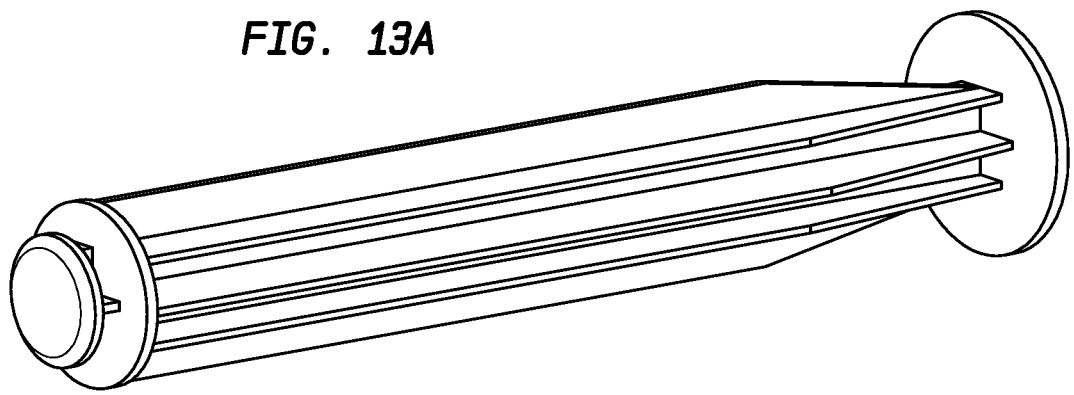
FIG. 13B
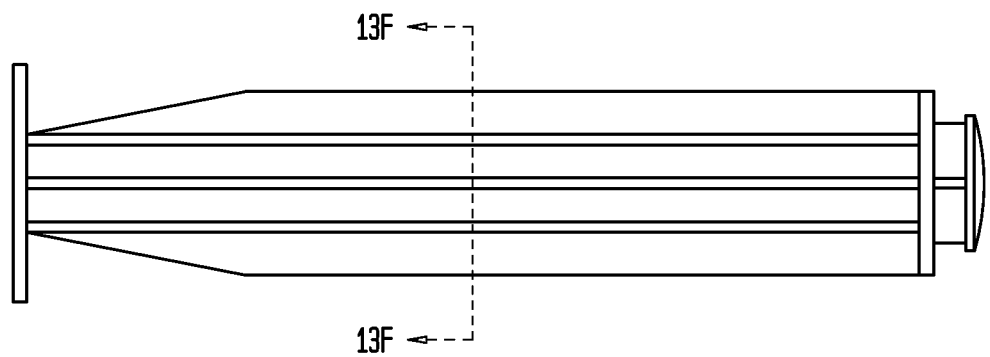
FIG. 13C
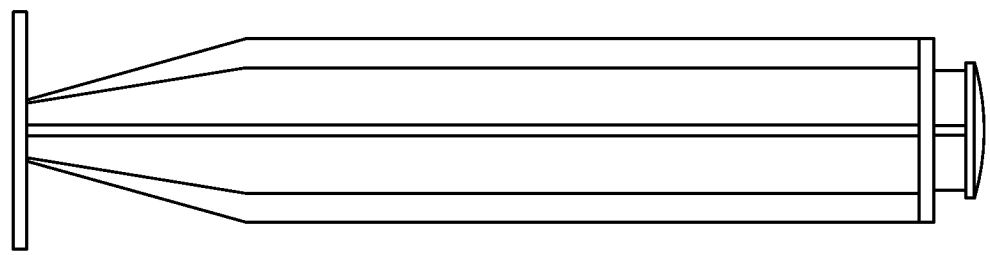
FIG. 13D  FIG. 13E  FIG. 13F
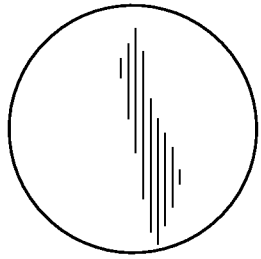 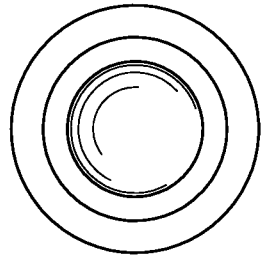 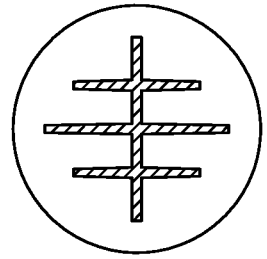

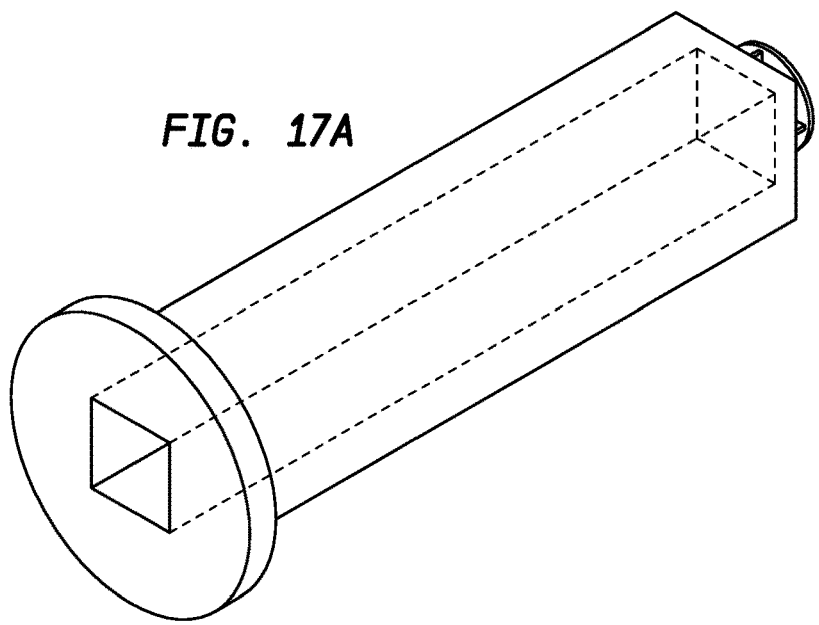
FIG. 17A
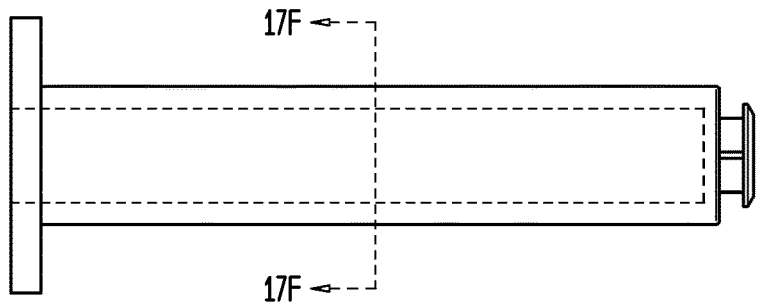
FIG. 17B
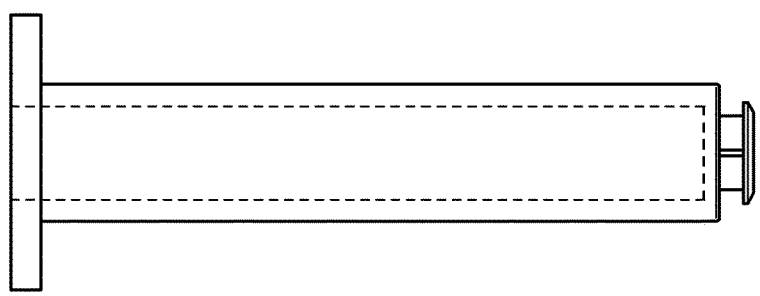
FIG. 17C
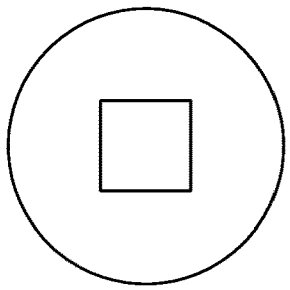 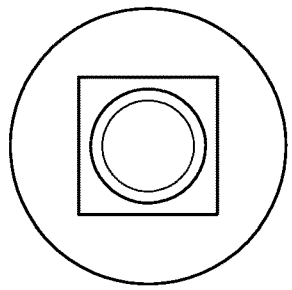 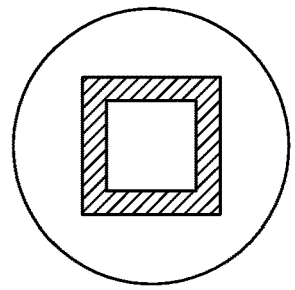
FIG. 17D    FIG. 17E    FIG. 17F

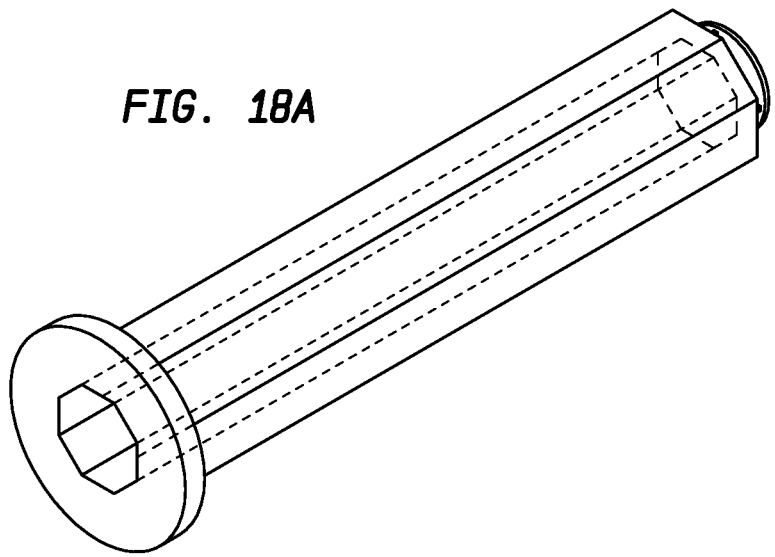
FIG. 18A
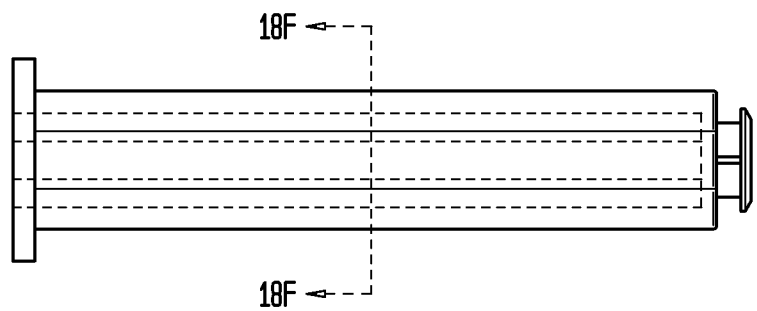
FIG. 18B
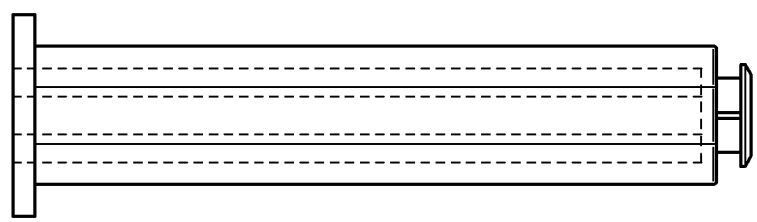
FIG. 18C
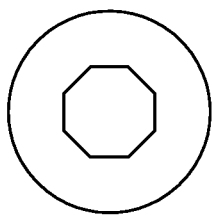 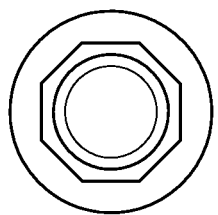 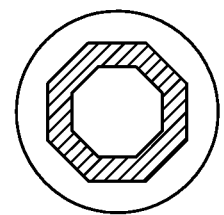
FIG. 18D     FIG. 18E     FIG. 18F

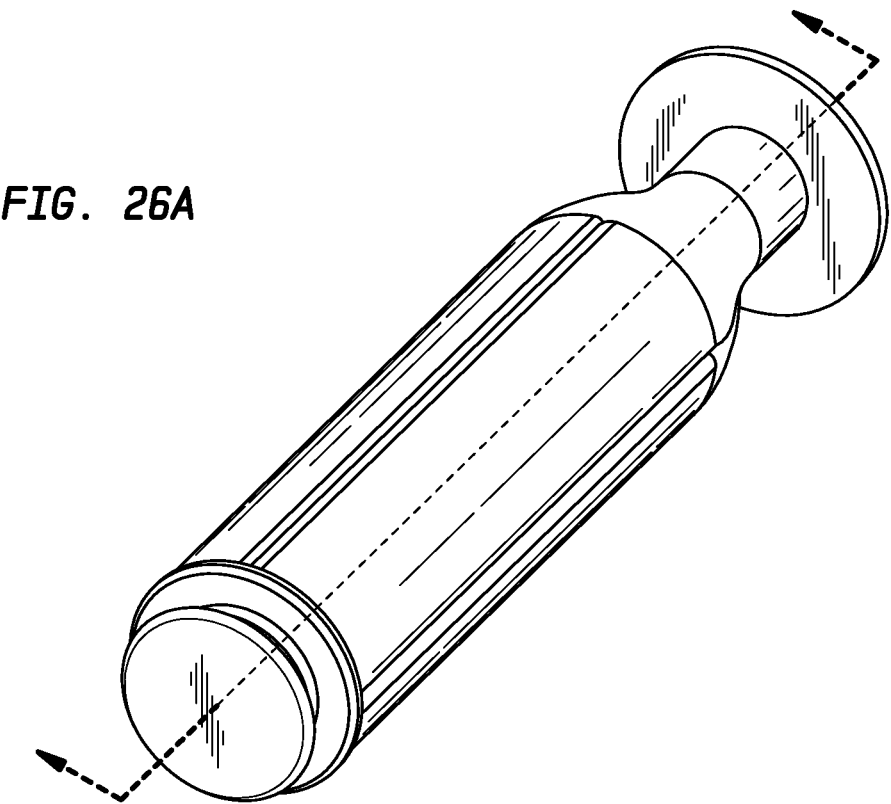
FIG. 26A
FIG. 26B
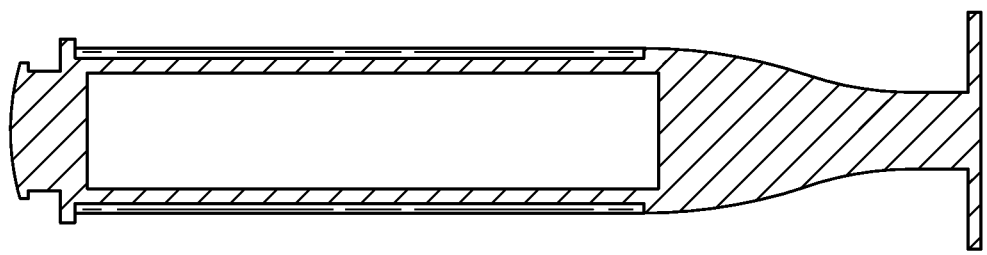

RECYCLED RESIN COMPOSITIONS AND DISPOSABLE MEDICAL DEVICES MADE THEREFROM

CROSS-REFERENCE TO RELATED APPLICATIONS

This application is a divisional of U.S. patent application Ser. No. 13/289,226, filed Nov. 4, 2011, the entire disclosure of which is hereby incorporated by reference herein.

BACKGROUND

The present invention relates to recycled resin compositions, medical devices formed from virgin material or recycled resin compositions and methods for manufacturing medical devices from virgin material or recycled resin compositions. Specifically, embodiments of the invention are directed to syringe plunger rods made from virgin material, recycled resin compositions, bio-based materials, or combinations thereof requiring less material while maintaining sufficient structural integrity to function properly.

Plastics form a significant portion of the majority of disposable medical devices, non-disposable medical devices, medical device packaging as well as other non-medical device applications including automotive and commodity applications. These include polymers such as polypropylene, polyethylene, polystyrene, polyethyleneterephthalate and polycarbonate among others. Increasing use of plastics over the past decades has resulted in increased impact on landfill capacity and the depletion of fossil fuel-based resources. Additionally, waste may also be incinerated, thereby creating a potential air pollution issue. The increasing use of plastics has also resulted in increasing level of environmental pollution, associated carbon footprint and other environmental impacts.

In light of above, there has been an increased interest in the utilization of recycled thermoplastic polymeric materials, which may be obtained from a variety of sources. The increased interest in utilizing recycled thermoplastic polymeric materials is driven by a number of factors, including increased customer awareness and concern for protection of the environment, environmentally preferred purchasing policies developed by customers, recognition of benefits of environmental stewardship in marketing by brand owners and by institutional customers who can market product themselves, development of new regulations and environmental policies intended to reduce the carbon footprint, and a desire to reduce the increasing costs of storage and/or landfill space coupled with more stringent regulations for disposal and incineration. The increased interest in utilizing recycled thermoplastic polymeric materials and thermoset materials is also driven by the improved capabilities of recyclers to consistently produce high quality recycled resins. These factors have already resulted in extensive use of recycled plastics in automotive and food packaging applications. For example, Ford Motor Company has developed ways to increase the use of recycled materials in its vehicle manufacturing. Two exemplary outcomes of this development include Visteon Automotive Systems' recycling of thermoplastic scrap from automobile bumpers and E.I. du Pont de Nemours and Company recycling of scrap into automobile air cleaners. Recycled PET or polyethylene terephthalate is extensively used in food and packaging applications including beverage bottles.

In order to enhance the environmental stewardship of medical devices and ability of healthcare organizations to satisfy environmental targets, for example, the LEED system while reducing the impact on landfills, without sacrificing safety, there is a growing emphasis on manufacturing medical devices made from recycled plastics. Potential issues with using recycled resins in manufacturing medical devices or their components include obstacles such as lack of biocompatibility, lot-to-lot variability in properties, and undesirable changes to the appearance during the sterilization process. Furthermore, when recycled resin compositions are used to form fluid-path-contact medical devices, there is a concern that the recycled resin compositions may have lot-to-lot variability, contamination, or may interfere with the material being transmitted, carried or delivered through the medical device.

Accordingly, there is a need in the industry for thermoplastic compositions comprised of recycled resin compositions that are biocompatible, sterilization-stable and useful for medical device applications. Such recycled resin compositions are not only limited to medical device applications and would apply to any industry that may utilize such compositions that are sterilization-stable.

SUMMARY

One or more embodiments of the invention are directed to syringe plunger rods comprising an elongate body, a thumbpress and a stopper support. The elongate body has a proximal end and a distal end defining a length. The elongate body being formed from a composition comprising one or more of a sterilization-stable recycled resin and a biobased composition. The thumbpress is positioned at the proximal end of the elongate body. The stopper support is positioned at the distal end of the elongate body.

In some embodiments, the elongate body comprises at least one rib extending the length of the elongate body, the at least one rib comprising a plurality of spaced openings. In detailed embodiments, the elongate body comprises four ribs in a plus shape. In specific embodiments, the plurality of spaced openings are along two of the four ribs.

In detailed embodiments, the elongate body comprises three ribs. In specific embodiments, the plurality of spaced openings are along two of the three ribs. In certain embodiments, the plurality of spaced openings are along one of the three ribs. In some embodiments, the elongate body comprises at least two ribs extending the length of the elongate body and the plurality of spaced openings are positioned on less than all of the ribs.

In detailed embodiments, the elongate body comprises two ribs in a v-shape with a plurality of support walls spaced along the length of the elongate body.

Some embodiments further comprise a plurality of support walls spaced along the length of the elongate body.

In one or more embodiment, the elongate body comprises a hollow portion. Specific embodiments further comprise at least one rib within the hollow extending at least partially along the length of the elongate body. In detailed embodiment, the hollow portion is shaped substantially similar to that of the elongate body.

In detailed embodiments, the syringe plunger rod is capable of withstanding sterilization comprising one or more of exposure to gamma rays in the range from about 5 kGys to about 75 kGys, exposure to an electron beam in the range from about 40 kGys to about 100 kGys, exposure to X-ray radiation and exposure to ethylene oxide gas, autoclaving, plasma sterilization. In specific embodiments, the composition comprises a recycled resin composition having from about 0.1% to about 100% by weight recycled resin selected from one of post-industrial recycled resin, post-consumer recycled resin and combinations thereof. In certain embodiments, the composition further comprises one or more of an antioxidant component, slip additive component, anti-static component, impact modifier component, colorant component, acid scavenger component, x-ray fluorescence agent component, radio-opaque filler component, surface modifier component, processing aid component, melt stabilizer, clarifiers and reinforcing agent component.

The syringe plunger rod of some embodiments exhibits a functional performance that is about the same or greater than the functional performance exhibited by plunger rods formed from a non-recycled resin composition. In detailed embodiments, the composition has a flexural modulus in the range from about 70 kpsi to about 300 kpsi. In specific embodiments, the composition has a melt flow range in the range from about 3 dg/minute to about 80 dg/minute. In certain embodiments, the composition has a heat deflection temperature from about 68° C. to about 140° C. In one or more embodiments, the composition has a notched izod impact strength in the range from about 0.2 ft-lb/in to about 3.0 ft-lb/in.

In some embodiments, the elongate body is cylindrical and there are a plurality of openings therethrough spaced along the length of the elongate body.

Additional embodiments of the invention are directed to a syringe plunger rod comprising an elongate body, a thumbpress and a stopper support. The elongate body has a proximal end and a distal end defining a length. The elongate body having at least one opening therethrough. The thumbpress is positioned at the proximal end of the elongate body. The stopper support is positioned at the distal end of the elongate body. The plunger rod is made from a composition comprising one or more of virgin material, sterilization-stable recycled resin and a biobased composition.

In some embodiments, the elongate body comprises at least one rib extending the length of the elongate body and a plurality of openings spaced along the length of the at least one rib. In detailed embodiments, the elongate body comprises a hollow portion along the length of the elongate body. Specific embodiments further comprise at least one rib extending within the hollow portion along at least a partial length of the elongate body.

BRIEF DESCRIPTION OF THE DRAWINGS

FIGS. 3A-3E illustrate a syringe plunger rod according to one or more embodiment of the invention;

FIGS. 6A-6F illustrate a syringe plunger rod according to one or more embodiment of the invention;

FIGS. 8A-8F illustrate a syringe plunger rod according to one or more embodiment of the invention;

FIGS. 12A-12F illustrate a syringe plunger rod according to one or more embodiment of the invention;

FIGS. 13A-13F illustrate a syringe plunger rod according to one or more embodiment of the invention;

FIGS. 17A-17F illustrate a syringe plunger rod according to one or more embodiment of the invention;

FIGS. 18A-18F illustrate a syringe plunger rod according to one or more embodiment of the invention;

FIG. 26A illustrates a syringe plunger rod according to one or more embodiment of the invention;

FIG. 26B illustrates a cross-section of the syringe plunger rod of FIG. 26A;

DETAILED DESCRIPTION

Figure 1:
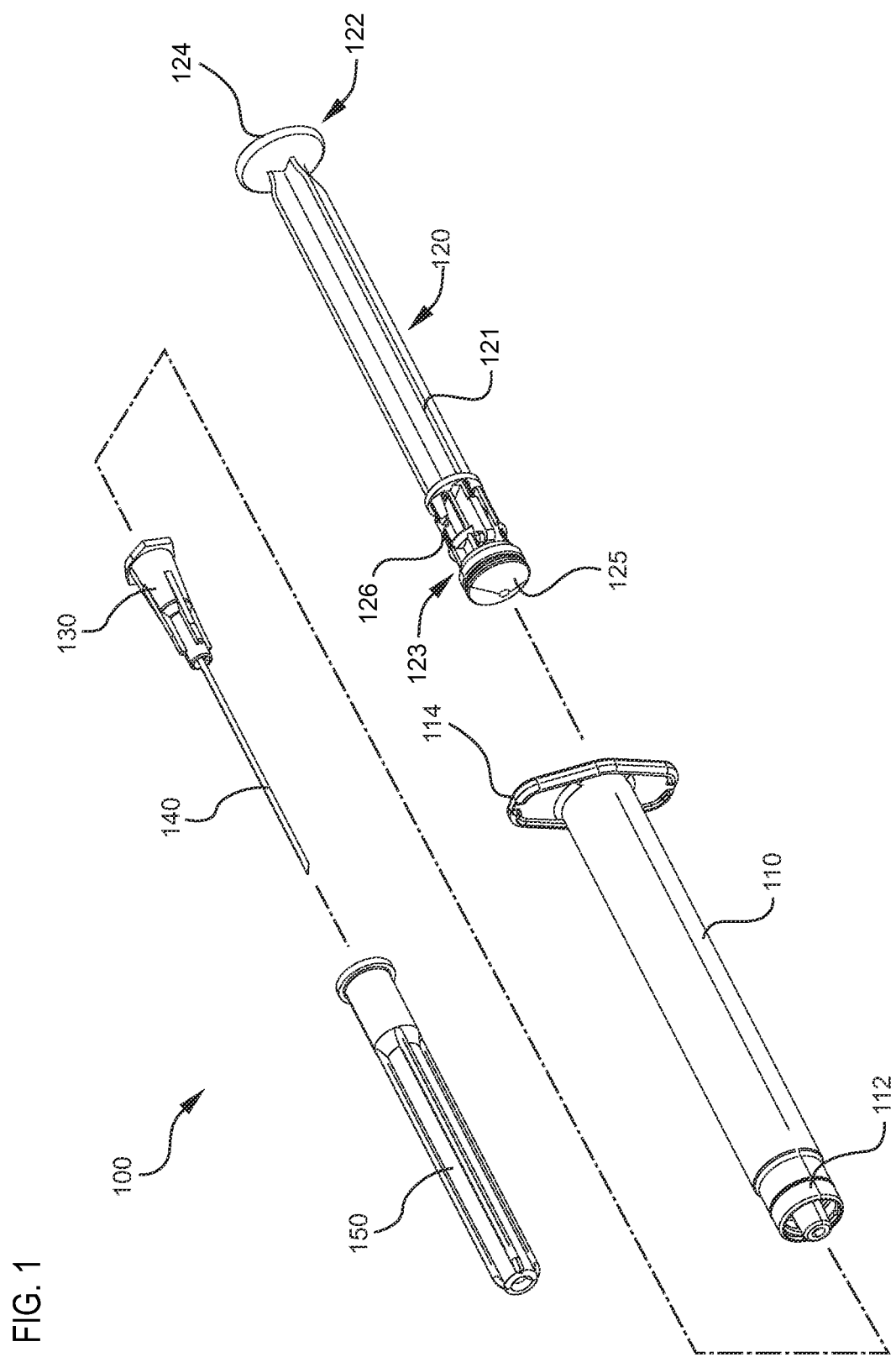
FIG. 1 illustrates an exploded view of a syringe assembly of one or more embodiments of the present invention.

Before describing several exemplary embodiments of the invention, it is to be understood that the invention is not limited to the details of construction or process steps set forth in the following description. The invention is capable of other embodiments and of being practiced or being carried out in various ways.

As used herein, the term "medical device" shall include all devices and components used in conjunction with other components in devices that are used in all medical and/or laboratory purposes, excluding waste collection containers such as sharps collection containers. Medical devices include syringe assemblies, including syringe barrels, plunger rods, catheters, needle hubs and needle shields, safety shields, surgical blades, surgical handles, sharps containers, body fluid collection devices, tubing, adapters, shunts, drainage tubes, guidewires, stents, petri dishes, culture bottles, centrifuge tubes, blood collection devices and the like. As indicated, as used herein "medical devices" excludes waste collection containers such as sharps collection containers.

As used herein, the term "biocompatible" shall mean any substance that is not toxic to the body or biological environment or does not produce an undesirable biological response during the period of exposure to the human body. Biocompatible compositions may also be compatible with petri dish and medical assay type applications (i.e., laboratory studies) so that the material does not interfere with the biological functions of organisms being used in studies. A composition is biocompatible if the composition, and any degradation products of the composition, are non-toxic to the recipient or biological environment and also present no significant deleterious effects on the biological environment, depending on the mode of use (e.g., short-term use or long-term use). A medical device is biocompatible if the medical device, and any degradation products of the medical device, are non-toxic to the recipient or biological environment and also present no significant deleterious effects on the biological environment. In detailed embodiments, biocompatible material meet the requirements of the U.S. Pharmacopeia and/or ISO 10993.

In addition, as used herein, the term "sterilization-stable" shall mean the ability of a medical device or component to withstand sterilization without significant loss of functional performance and mechanical properties. Sterilization includes exposure to radiation, for example, gamma rays and/or X-rays, during the sterilization process. Medical devices or components thereof that are capable of withstanding radiation sterilization without significant loss of functional performance may be referred to as "radiation stable." An example of a sterilization process may include exposure of a medical device to high energy photons that are emitted from an isotope source, for example Cobalt 60, which produces ionization or electron disruptions throughout the medical device. Sterilization may also include ethylene oxide sterilization, electron beam sterilization, autoclave (steam sterilization), plasma sterilization, dry heat sterilization, chemical sterilization, and X-ray beam sterilization.

As used herein, "fluid path contact medical devices" are medical devices wherein at least a portion of the medical device comes into contact or interacts with fluids and/or solids, for example, medications, solutions of medications, drug containing solutions, flush solutions, body fluids, human tissue, or any material that is intended to be isolated to prevent contamination. As used herein, reference to a medical device "formed from a sterilization-stable recycled resin composition" means that the device is manufactured, for example, shaped from a resin obtained from recycled resin. Accordingly, a medical device "formed from a sterilization-stable recycled resin composition" does not include a medical device that is used, and then reprocessed by cleaning or sterilization of a part of or the entire device by radiation or in an autoclave. Such reuse of medical device is often referred to as "reprocessing", and reprocessed medical devices are not within the scope of a device formed from a sterilization-stable recycled resin composition because such reprocessing does not include shaping or other manufacturing process to form a device from a resin composition.

A first aspect of the present invention pertains to compositions for use in molding a medical device that includes a recycled resin from a traceable source. A second aspect of the present invention pertains to a medical device that is formed from a recycled resin composition. A third aspect of the present invention pertains to a method of forming a medical device.

The medical devices, including the syringe plunger rods described, can be made from a composition comprising one or more of virgin material, sterilization-stable recycled resin and a biobased composition. The composition can contain single components having mixed sources (e.g., the same type of plastic with a mixture of virgin material and recycled material) or multiple components from the same source (e.g., two types of plastics with both being virgin material).

The recycled resin compositions of one or more embodiments of the first aspect may include a post-industrial recycled resin. The amount of post-industrial recycled resin may be present in the recycled resin composition in the range from about 0.1% to about 100% by weight of the recycled resin composition. In one or more embodiments, the recycled resin composition includes post-industrial recycled resin in an amount in the range from about 50% to about 99% by weight. In one or more specific embodiments, the recycled resin composition may include post-industrial recycled resin in an amount in the range from about 20% to about 80% by weight. In a more specific embodiment, the lower limit of the amount of post-industrial recycled resin may include 25%, 30%, 35%, 40%, 45% and 50% by weight of the recycled resin composition and all ranges and sub-ranges therebetween. The upper limit of the amount of post-industrial recycled resin may include 75%, 70%, 65%, 60%, 55% and 50% by weight of the recycled resin composition and all ranges and sub-ranges therebetween.

The recycled resin compositions of one or more embodiments of the first aspect may include a post-consumer recycled resin. The resin may be provided in any suitable form, such as in the form of flakes, chips, pellets and the like. In one variant, the recycled resin compositions may include post-consumer recycled resin and post-industrial recycled resin. The amount of post-consumer recycled resin may be present in the recycled resin composition in the range from about 0.1% to about 100% by weight of the recycled resin composition. In one or more embodiments, the recycled resin composition includes post-consumer recycled resin in an amount in the range from about 50% to about 99% by weight. In one or more specific embodiments, the recycled resin composition may include post-consumer recycled resin in an amount in the range from about 20% to about 80% by weight. In a more specific embodiment, the lower limit of the amount of post-consumer recycled resin may include 25%, 30%, 35%, 40%, 45% and 50% by weight of the recycled resin composition and all ranges and sub-ranges therebetween. The upper limit of the amount of post-consumer recycled resin may include 75%, 70%, 65%, 60%, 55% and 50% by weight of the recycled resin composition and all ranges and sub-ranges therebetween.

Examples of suitable post-industrial recycled resins and post-consumer recycled resins include polypropylene, polycarbonates, nylons, polyethyleneterphthalates, polyesters, polyethylenes, polystyrenes, poly lactic acid, polyhydroxyalkanoates, bioderived polyolefins including polyethylene and polypropylene and other resins known in the art that are recyclable and combinations thereof. The recycled resins may have been recovered or otherwise diverted from the solid waste stream, either during the manufacturing process (pre-consumer), or after consumer use (post-consumer).

In one or more embodiments, the recycled resin composition may also include one or more of the optional additives. These optional additives are selected from the group consisting of anti-oxidants, slip additives, anti-static agents, impact modifiers, plasticizers, surface-active agents, colorants, acid scavengers, X-ray fluorescence agents, radioopaque fillers, surface modifiers, processing aids including melt stabilizers, nucleating agents including clarifiers, flame retardants, inorganic fillers other than finely powdered talc, organic fillers and other polymers and reinforcing agents.

In one or more embodiments, the recycled resin composition includes an anti-oxidant component. The anti-oxidant component may include chemical compounds that inhibit oxidation via chain terminating reactions. In one or more embodiments, the anti-oxidant component may be present in the recycled resin composition in an amount up to about 10% by weight of the recycled resin composition. In one or more specific embodiments, the recycled resin composition may include an anti-oxidant component in an amount of up to about 5% by weight or, more specifically, an amount of up to about 1% by weight of the recycled resin composition. In one or more specific embodiments, the anti-oxidant component may be present in an amount in the range from about 1% by weight to about 5% by weight of the recycled resin composition. In an even more specific embodiment, the anti-oxidant component may be present in an amount in the range from about 0.1% to about 1% by weight of the recycled resin composition. The upper limit of the amount of the anti-oxidant component may include 0.9%, 0.8%, 0.7%, 0.6% and 0.5% and all ranges and sub-ranges therebetween.

In one or more embodiments, the anti-oxidant component is present in an amount sufficient to inhibit oxidation reactions during sterilization and over the shelf life and/or use-phase of the product.

Non-exclusive examples of suitable anti-oxidant components include hindered phenols, hindered amines, phosphites and/or combinations thereof. Hindered phenols include chemical compounds that act as hydrogen donors and react with peroxy radicals to form hydroperoxides and prevent the abstraction of hydrogen from the polymer backbone. Suitable hindered phenols include buylated hydroxytoluene. Other suitable hindered phenols are available under the trademark Irganox® 1076, Irganox® 1010, Irganox® 3114 and Irganox®E 201, from Ciba, Inc., now part of BASF Corporation of Ludwigshafen, Germany. Other examples of hindered phenols include BNX®1010 and BNX®1076TF from Mayzo Inc. or Norcross, Ga., U.S.A. Suitable hindered phenols are also available under the trademark Ethanox®330 and Ethanox®376 from Albemarle Corporation of Baton Rouge, La., U.S.A.

Hindered amines include chemical compounds containing an amine functional group surrounded by a steric environment. They are extremely efficient stabilizers against light-induced degradation of most polymers. Examples of suitable hindered amines include bis(1,2,2,6,6-pentamethyl-4-piperidinyl)-2-n-butyl-2-(3,5-di-tert-butyl-4-hydroxybenzyl) malonate; bis(2,2,6,6-tetramethyl-4-piperidinyl)sebacate, bis(1,2,3,6,6-pentamethyl-4-piperidinyl)sebacate and bis(1, 2,2,6,6-pentamethyl-4-piperidinyl)sebacate. These are commonly referred to as Tinuvin 144, Tinuvin 770, Tinuvin 292 and Tinuvin 765 respectively and are available from the Ciba-Geigy Corporation, now part of BASF Corporation of Ludwigshafen, Germany. Other examples of suitable hindered amines are available under the tradenames Uvasorb HA-88 from 3V Sigma SpA of Bergamo, Italy, and Chimassorb 944 and Chimassorb 994 from BASF Corporation of Ludwigshafen, Germany.

In specific embodiments, the recycled resin composition includes a slip additive component. The slip additive component may include chemical compounds that reduce the surface coefficient of friction of polymers and are used to enhance either processing or end applications. The slip additive component may be present in the recycled resin composition in an amount in the range from about 0.001% to about 5% by weight of the recycled resin composition and all ranges and sub-ranges therebetween. In one or more specific embodiments, the slip additive component is present in an amount in the range from about 1% to about 2% by weight of the recycled resin composition. The upper limit of the amount of the slip additive component may include 4.5%, 4.0%, 3.5%, 3.0%, and 2.5% by weight of the recycled resin composition and all ranges and sub-ranges therebetween. The lower limit of the amount of the slip additive component may include 0.1%, 0.2%, 0.3%, 0.4%, 0.5%, 0.6%, 0.7%, 0.8%, and 0.9% by weight of the recycled resin composition and all ranges and sub-ranges therebetween. Examples of suitable slip additive components include oleamides, erucamide, Oleyl palmitamide, Stearyl erucamide, Ethylene-bis-oleamide, waxes and combinations thereof.

The recycled resin composition optionally includes an anti-static component. The anti-static component may include chemical compounds that prevent or reduce the accumulation of static electricity. The anti-static component acts to permit the body or surface of the material to be static dissipative, preventing the formation of static charges and hindering the fixation of dust. The anti-static component may be incorporated in the material before molding, or applied to the surface after molding and function either by being inherently static dissipative or by absorbing moisture from the air. The anti-static component may be present in the recycled resin composition in an amount in the range from about 0.01% to about 5% by weight of the recycled resin composition and all ranges and sub-ranges therebetween. In one or more specific embodiments, the anti-static component is present in an amount in the range from about 0.1% to about 3.0% by weight of the recycled resin composition and all ranges and sub-ranges therebetween. The upper limit of the amount of the anti-static component may include 4.5%, 4.0%, 3.5%, 3.0% and 2.5% by weight of the recycled resin composition and all ranges and sub-ranges therebetween. The lower limit of the amount of the anti-static component may include 0.1%, 0.2%, 0.3%, 0.4%, 0.5%, 0.6%, 0.7%, 0.8%, 0.9% and 1.0% by weight of the recycled resin composition and all ranges and sub-ranges therebetween. Examples of anti-static agent components are long-chain aliphatic amines and amides, phosphate esters, quaternary ammonium salts, polyethylene glycols, polyethylene glycol esters, ethoxylated long-chained aliphatic amines and combinations thereof. Other examples of suitable anti-static agents are available under the trade name Pelestat 230 and Pelestat 300 from Toyota Tsusho Corporation of Nagoya, Japan, Atmer™ 163 from Uniqema, now part of Croda International Plc of Yorkshire, England, U.K, Entira™ MK 400 from E.I DuPont de Nemours and Company of Wilmington, Del., U.S.A and Nourymix® AP 375 and 775 from Akzo Nobel N.V. of Amsterdam, the Netherlands.

The recycled resin composition optionally includes an impact modifier component. The impact modifier component may include chemical compounds for improving the impact resistance of finished articles or devices. The impact modifier component may be present in the recycled resin composition in an amount in the range from about 0.1% to about 30% by weight of the recycled resin composition. In one or more specific embodiments, the impact modifier component is present in an amount in the range from about 0.5% to about 5% by weight of the recycled resin composition and all ranges and sub-ranges therebetween. The upper limit of the amount of impact modifier component may include 4.5%, 4.0%, 3.5%, 3.0%, 2.5% and 2.0% by weight of the recycled resin composition and all ranges and sub-ranges therebetween. The lower limit of the amount of impact modifier component may include 0.75%, 1.0%, 1.25%, 1.5%, 1.75% and 2.0% by weight of the recycled resin composition and all ranges and sub-ranges therebetween. Examples of suitable impact modifier components include ethylene-butene copolymers, ethylene octene copolymers, ethylene-propylene copolymers, methacrylate butadiene-styrene core shell impact modifiers and combinations thereof. Examples of suitable impact modifier agents are available under the trade name Elvaloy® EAC3427 from E.I DuPont de Nemours and Company of Wilmington, Del., U.S.A., Engage™ and Versify™ from the Dow Chemical Company of Midland, Mich., U.S.A. and Clearstrength™ from Arkema Inc. of Philadelphia, Pa., U.S.A.

When present, the impact modifier component can be present in an amount sufficient to meet the impact requirements of the fabricated medical article.

The recycled resin composition optionally includes an acid scavenger component. The acid scavenger component may include chemical compounds for preventing discoloration or premature aging of the polymer as well as the fabricated medical article from the acidic impurities during the course of manufacturing, processing, sterilization, shelf life or use phase. For example, such chemical compounds may neutralize halogen anions found in resin compositions that may be formed due to the influence of heat and shear during processing. The acid scavenger component scavenges these halogenic acids to prevent polymer degradation or corrosion. The acid scavenger component may be present in the recycled resin composition in an amount in the range from about 0.01% to about 1% by weight of the recycled resin composition. In one or more specific embodiments, the acid scavenger component is present in an amount in the range from about 0.1% to about 0.5% by weight of the recycled resin composition and all ranges and sub-ranges therebetween. The upper limit of the amount of acid scavenger component may include 0.6%, 0.7%, 0.8%, and 0.9% by weight of the recycled resin composition and all ranges and sub-ranges therebetween. The lower limit of the amount of acid scavenger component may include 0.01%, 0.02%, 0.03%, 0.04%. 0.05%, 0.06%. 0.07%, 0.08% and 0.09% by weight of the recycled resin composition and all ranges and sub-ranges therebetween. Examples of suitable acid scavenger components include metal salts of long chain carboxylic acids like calcium, zinc or sodium stearates, lactates, natural or synthetic silicates like hydrotalcites, metal oxides (e.g. magnesium oxide, calcium oxide, zinc oxide), metal carbonates (e.g. calcium carbonate) or metal hydroxides (see e.g. A Holzner, K Chmil in H. Zweifel, Plastic Additives Handbook, 5$^{th}$ Ed., Hanser Publisher, Munich 2001, Chapter 4 Acid Scavengers). Suitable examples of acid scavengers include calcium stearate, dihydro talcite, calcium lactate, mono potassium citrate and combinations thereof.

When present, the acid scavenger component can be present in the recycled resin composition in an amount sufficient to inhibit discoloration and prevent degradation caused by acidic impurities during manufacturing, processing, storage, shelf life or use phase of polymer and medical article fabricated therefrom.

Another optional component of the recycled resin composition is a radio-opaque filler component. The radio-opaque filler component may include chemical compounds that cause medical devices formed from the resin composition to be visible under fluoroscopy or x-ray imaging. The radio-opaque filler component may be present in the recycled resin composition in an amount in the range from about 10% to about 48% by weight of the recycled resin composition and all ranges and sub-ranges therebetween. In one or more specific embodiments, the radio-opaque filler component is present in an amount in the range from about 22% to about 25% by weight of the recycled resin composition and all ranges and sub-ranges therebetween. The upper limit of the amount of the radio-opaque filler component may include 26%, 28%, 30%, 32%, 34%, 36%, 38%, 40%, 42%, 44% and 46% by weight of the recycled resin composition and all ranges and subranges therebetween. The lower limit of the amount of the radio-opaque filler component may include 11%, 12%, 13%, 14%, 15%, 16%, 17%, 18%, 19% and 20% by weight of the recycled resin composition and all ranges and subranges therebetween. Higher percentages of radio-opaque filler component may also be used. For example, the amount of the radio-opaque filler component may be more than about 50% by weight of the recycled resin composition. Examples of suitable radio-opaque filler components include barium sulfate, bismuth subcarbonate, bismuth trioxide, bismuth oxychloride, tungsten and combinations thereof.

The radio-opaque filler component can be present in an amount sufficient to enable visibility of the medical devices using x-ray and other radiology imaging techniques.

The recycled resin composition further optionally includes a surface modifier component. The surface modifier component may include chemical compounds or materials which tailor the surface of the fabricated component(s) to meet or enhance adhesion, lubricity and/or physical properties. The surface modifier component may be present in the recycled resin composition in an amount in the range from about 0.1% to about 10% by weight of the recycled resin composition. In one or more specific embodiments, the surface modifier component is present in an amount in the range from about 0.5% to about 5%, more preferably between 0.2 to 1% by weight of the recycled resin composition and all ranges and sub-ranges therebetween. The upper limit of the amount of the surface modifier component may include 1.5%, 2.0%, 3.0%, 3.5%, 4.0% and 4.5% and all ranges and sub-ranges therebetween. The lower limit of the amount of the surface modifier component may include 0.3%, 0.35%, 0.4% and 0.45% by weight of the recycled resin composition and all ranges and sub-ranges therebetween. In one or more embodiments, higher percentages of surface modifiers may also be used. Examples of suitable surface modifier components include diatomaceous earth, talc, calcium carbonate, organosilanes, titanates, maleated polyolefins, powdered PTFE and combinations thereof.

The surface modifier can be present in the recycled resin composition in an amount sufficient to impart desirable surface property to the surface of the fabricated medical device.

In one or more embodiments, the recycled resin composition includes a colorant component. The colorant component may be present in the recycled resin composition in an amount in the range from about 0.01% to about 5% by weight of the recycled resin composition. In one or more specific embodiments, the colorant component(s) are present in an amount in the range from about 0.5% to about 3% by weight of the recycled resin composition and all ranges and sub-ranges therebetween. The upper limit of the amount of colorant component may include 3.25%, 3.5%, 3.75%, 4.0%, 4.25%, 4.5% and 4.75% by weight of the recycled resin composition and all ranges and sub-ranges therebetween. The lower limit of the amount of the colorant component may include 0.1%, 0.15%, 0.2%, 0.25%, 0.3%, 0.35%, 0.4% and 0.45% by weight of the recycled resin composition and all ranges and sub-ranges therebetween. Examples of suitable colorant components include organic dyes, inorganic pigments, carbon black, channel black, titanium dioxide and combinations thereof. Organic dyes may include Phthalocyanine blue and Phthalocyanine green, and FD&C colorants. Exemplary inorganic pigments include ultramarines and iron oxides.

Another optional component of the recycled resin composition includes a processing aid component. The processing aid component may include chemical compounds which improve the processability of high molecular weight polymers, reduces the cycle time and help improve quality of finished products. The processing aid component may be present in the recycled resin composition in an amount in the range from about 0.05% to about 5% by weight of the recycled resin composition and all ranges and sub-ranges therebetween. In one or more specific embodiments, the processing aid component is present in an amount in the range from about 0.1 to about 3% by weight of the recycled resin composition and all ranges and sub-ranges therebetween. The upper limit of the amount of colorant component may include 3.25%, 3.5%, 3.75%, 4.0%, 4.25%, 4.5% and 4.75% by weight of the recycled resin composition and all ranges and sub-ranges therebetween. The lower limit of the amount of the colorant component may include 0.06%, 0.07%, 0.08% and 0.09% by weight of the recycled resin composition and all ranges and sub-ranges therebetween. Higher percentages of processing aid may also be used. Examples of suitable processing aid components include fatty acid esters, fatty acid amines, waxes, oxidized polyethylenes, colloidal fumed silica particles and combinations thereof. Colloidal fumed silica particles are available under the tradename Nan-O-Sil ASD from Energy Strategy Associates, Inc. of Old Chatham, N.Y., USA and other suppliers. Glycerol monostearates and bisstearaamides are suitable fatty acid esters and fatty acid amides.

The recycled resin composition may optionally include a nucleating agents and/or clarifier component. Nucleating agents may include chemical compounds that enhance resin performance properties such as stiffness and heat resistance. A clarifier may also be added to enhance the aesthetic appeal of a formed product by making it more transparent. In one or more embodiments, the nucleating and/or clarifier component is present in an amount in the range from about 0.005% to about 3% by weight of the recycled resin composition. Higher percentages of nucleating and/or clarifying agents may be used but generally provide no perceived advantages. In one or more specific embodiments, the clarifier component is present in an amount in the range from about 0.05 to about 0.5% by weight of the recycled resin composition and all ranges and sub-ranges therebetween. The upper limit of the amount of the clarifier component may include 1.0%, 1.5%, 2.0% and 2.5% by weight of the recycled resin composition and all ranges and sub-ranges therebetween. The lower limit of the amount of the clarifier component may include 0.01%, 0.015%, 0.02%, 0.025%, 0.03%, 0.035%, 0.04% and 0.045% by weight of the recycled resin composition and all ranges and sub-ranges therebetween. Examples of clarifier components include dibenzylidene sorbitol as described in U.S. Pat. No. 4,016,118, which is incorporated herein by reference, substituted dibenzylidene sorbitol as described in U.S. Pat. No. 4,371,645, which is incorporated herein by reference, and dibenzylidene sorbitol thioether derivatives as described in U.S. Pat. No. 4,994,552, which is incorporated herein by reference.

When present, the clarifiers can be present in an amount sufficient such that the size of the crystals in the resulting resin composition is smaller than the wavelength of visible light to prevent light scattering, which causes opacity.

The recycled resin composition optionally includes a reinforcing agent component. The reinforcing agent component may be present in the recycled resin composition in an amount in the range from about 1% to about 35% by weight of the recycled resin composition. In one or more specific embodiments, the reinforcing agent component(s) are present in an amount in the range from about 5% to about 30% by weight of the recycled resin composition and all ranges and sub-ranges therebetween. The upper limit of the amount of the reinforcing agent component may include 30.5%, 31%, 31.5%, 32%, 32.5%, 33%, 33.5%, 34% and 34.5% by weight of the recycled resin composition and all ranges and sub-ranges therebetween. The lower limit of the amount of the reinforcing agent component may include 1.5%, 2%, 2.5%, 3%, 3.5%, 4% and 4.5% by weight of the recycled resin composition and all ranges and sub-ranges therebetween. Examples of suitable reinforcing agent components include glass fibers, cinderash, natural fibers and minerals, carbon fibers, ceramic fibers, and combinations thereof. Examples of natural fibers include flax fibers and kenaf fibers and fillers, which are biobased materials. The reinforcing agent component may be present in the recycled resin composition in the form of nanofibers and/or nanoparticles.

The recycled resin composition according to one or more embodiments may optionally include a melt stabilizer component. The melt stabilizer component may include chemical compounds for adjusting the viscosity of the recycled resin composition during a melting process.

The recycled resin composition may also optionally incorporate a non-recycled resin component. Examples of a non-recycled resin component include virgin resin components, biobased resin components and combinations thereof. Virgin resin components are resin compositions that do not include a significant amount of recycled resin. In one or more embodiments, virgin resin components are free of recycled resin. Virgin resin components may also include "fossil fuel-based polymers" or "petroleum based polymers," which shall be used interchangeably, and include, without limitation, polymers formed from non-renewable sources such as fossil fuel sources. Such polymers include polypropylene, polyethylene not derived from sugar or other renewable resources, polycarbonate.

The term "biobased" may be used interchangeably with the terms "bioformed" and "bioderived." The biobased component includes components that are derived, produced or synthesized in whole or in significant part, from biological sources or renewable domestic agricultural materials (including plant, animal, and marine materials) or forestry materials. For example, the biobased component can include polymers in which carbon is derived from a renewable resource via biological processes such as microbiological fermentation. The biobased component may also include polymers with cellulose-based materials of different grades. The biobased component may also include polymers are that substantially free of materials derived from fossil fuel or non-renewable resources as determined by ASTM D6866-08.

The biobased component used herein may include polymers which are derived from biological sources, such as plants, and include polysaccharide-derived polymers, such as starch- or carbohydrate-derived polymers, and sugar-derived polymers. The starch used to form bioformed polymers may be derived from corn, potatoes, wheat, cassava, rice and other plants. An example of a composition containing bioformed polymer derived from starch is available from Cereplast Inc., Hawthorne, Calif., U.S.A., under the trademarks and trade names Cereplast Hybrid Resins®, Biopolyolefins®, or Biopropylene 50™. The sugar used to form such bioformed polymers may be derived from sugar cane. Such sugar-derived polymers include polyethylene, which may be produced from ethanol derived from sugar cane, which is then used to produce ethylene and polymers are available from Novamount S.P.A., Novara, Italy under the trademark MATER-BI®. Other examples of bioformed polymers are described in U.S. Pat. No. 7,393,590, U.S. Patent Application Publication Nos. 2008/0113887 and 2008/0153940, PCT Application Publication Nos. WO07/099427 and WO07/063361 and European Patent No. 1725614, each of which is incorporated herein in their entirety by reference. A specific example of a bioformed polymer includes "poly(lactic acid)" or "PLA," which may include a synthetic polymer produced from cane sugar or cornstarch. PLA is available from NatureWorks LLC, Minnetonka, Minn., U.S.A., under the trade name Ingeo™. Embodiments utilizing PLA may also include an ethylene copolymer. Ethylene copolymers are available from E.I. du Pont de Nemours and Company, Wilmington, Del., U.S.A., under the trademark BIOMAX®.

Biobased component includes polymers may also be produced from microbes. Microorganisms produce substances, including polymers, by growth on feedstock, including sugar feedstock. The production of these polymers may also involve bacterial fermentation of sugar or lipids. The biobased component may be further treated or synthesized from natural products. Examples of such produced and/or synthesized biobased polymers include polyhydroxyalkanoates The term "polyhydroxyalkanoate" or "PHA" includes linear polyesters produced in nature by bacterial fermentation of sugar or lipids. Examples of PHAs include poly(hydroxybutyrate) and poly(hydroxyvalerate) or "PHBV." PHAs may exhibit properties such as elasticity. PHAs are available from Metabolix, Inc., Cambridge, Mass., U.S.A., under the trademark MIREL®.

Recycled resin compositions according to one or more embodiments, are biocompatible, as defined herein. In one or more embodiments, the recycled resin composition is capable of withstanding exposure to gamma rays, electron beams, X-rays, ethylene oxide gas, dry heat, peroxide gas plasma, peracetic acid, steam autoclave and other means of sterilization. In one or more embodiments, the recycled resin composition is radiation stable and capable of withstanding exposure to gamma rays in the range from about 5 kGys to about 75 kGys, or more specifically, in the range from about 25 kGys to about 50 kGys. In one or more embodiments, the recycled resin composition is capable of withstanding exposure to electron beams in the range from about 30 kGys to about 80 kGys, or, more specifically, in the range from about 40 kGys to about 70 kGys.

The recycled resin composition according to one or more embodiments has a melt flow rate in the range from about 3 dg/minute to about 80 dg/minute. In one or more specific embodiments, the recycled resin composition has a melt flow rate in the range from about 8 dg/minute to about 40 dg/minute. In even more specific embodiments, the recycled resin composition has a melt flow rate in the range from about 11 dg/minute to about 30 dg/minute. As used herein, the term "melt flow rate" refers to the ease of flow of the melt of the recycled resin compositions described herein.

The recycled resin compositions described herein may have a flexural modulus in the range from about 70 kpsi to 350 kpsi and all ranges and subranges therebetween as measured according to ASTM D790 test method. In detailed embodiments, the recycled resin composition has a flexural modulus in the range of about 75 kpsi to about 300 kpsi. In one or more specific embodiments, the recycled resin compositions have a flexural modulus in the range from about 100 kpsi to about 300 kpsi. In even more specific embodiments, the recycled resin compositions exhibits a flexural modulus in the range from about 130 kpsi to about 270 kpsi.

The recycled resin composition may be characterized by having notched izod impact strength in the range from about 0.1 ft-lb/in. to about 4.0 ft-lb/in and all ranges and subranges as measured according to ASTM D256 test method. In one or more embodiments, the recycled resin composition may have notched izod impact strength in the range from about 0.2 ft-lb/in. to about 3.0 Ft-lb/in or in the range of about 0.2 ft-lm/in to about 1.5 ft-lb/in. In one or more specific embodiments, the recycled resin composition may have a notched izod impact strength in the range from about 0.3 ft-lb/in. to about 1.0 ft-lb/in. As used herein, the term "notched izod impact strength" refers to the ASTM standard method of determining impact strength.

One or more embodiments of the recycled resin composition described herein may be characterized by having a heat deflection temperature in the range from about 60° C. to about 260° C. As used herein, the term "heat deflection temperature" includes a measure of a polymer's resistance to distortion under a given load at elevated temperature. The heat deflection temperature is also known as the 'deflection temperature under load' (DTUL), deflection temperature, or 'heat distortion temperature' (HDT). The two common loads used to determine heat deflection temperature are 0.46 MPa (66 psi) and 1.8 MPa (264 psi), although tests performed at higher loads such as 5.0 MPa (725 psi) or 8.0 MPa (1160 psi) are occasionally encountered. The common ASTM test is ASTM D 648 while the analogous ISO test is ISO 75. The test using a 1.8 MPa load is performed under ISO 75 Method A while the test using a 0.46 MPa load is performed under ISO 75 Method B. In one or more specific embodiments, the recycled resin composition may have a heat deflection temperature in the range from about 68° C. to about 140° C., or in the range of about 68° C. to about 130° C. In even more specific embodiments, the recycled resin composition may have a heat deflection temperature in the range from about 70° C. to about 95° C. In one or more embodiments which utilize a post-industrial recycled resin component comprising polycarbonate, the recycled resin composition has a heat deflection temperature of about 140° C. at a load of 0.46 MPa and 130° C. at a load of 1.8 MPa. In one or more embodiments which utilize a post-industrial recycled resin component comprising nylon and a reinforcing agent component including glass fibers, the recycled resin composition has a heat deflection temperature of about 220° C. at a load of 0.46 MPa and 200° C. at a load of 1.8 MPa. In embodiments which utilize a post-industrial recycled resin component comprising PET and a reinforcing agent component including glass fibers, the recycled resin composition has a heat deflection temperature of about 250° C. at a load of 0.46 MPa and 230° C. at a load of 1.8 MPa.

Preparation of the recycled resin compositions of this invention can be accomplished by any suitable blending or mixing means known in the art. The blending step should, at least minimally, disperse the components amongst each other. The components may be blended together in a one-step process or a multi-step process. In the one-step process, all the components are blended together at the same time. In the multiple-step process, two or more components are blended together to form a first mixture and then one or more of the remaining components are blended with the first mixture. If one or more components still remain, these components may be blended in subsequent mixing steps. In one or more embodiments, all the components are blended in a single step.

In one or more alternative embodiments, the recycled polypropylene composition may be prepared by dry blending the individual components and subsequently melt mixing, either directly in the extruder used to make the finished article, or premixing in a separate extruder. Dry blends of the composition may also be directly injection molded without pre-melt mixing.

The recycled resin compositions disclosed herein are utilized to mold, extrude or otherwise form a medical device. In one or more embodiments, the medical device is disposable. For example, the medical devices may be formed from the recycled resin compositions described herein may be used in injection, infusion, blood collection, surgical applications and other applications known in the art. Specific examples of medical devices that may be formed form the recycled resin compositions described herein include syringes (including syringe barrels, needle hub parts, plunger rods, needle shields and the like), safety syringes, catheters, blood collection devices, surgical blades or scalpels and other such devices and components. In one or more alternative embodiments, the medical device may be entirely or partially molded from a recycled resin composition. For example, the inside surface of a syringe barrel may be formed from a resin composition that is not recycled while the outside surface of the syringe barrel or the finger flanges of the syringe barrel are made from a recycled resin composition. In one or more alternative embodiments, the scalpel handle or needle shield are formed from a recycled resin composition.

In one or more embodiments, the medical devices formed from the recycled resin compositions described herein may be characterized as non-fluid path contact components or medical devices. As such, the medical devices and components do not interact or come into contact with fluids and/or solids, for example, medications, solutions of medications, drug containing solutions, flush solutions, body fluids, human tissue, or any material that is intended to be isolated to prevent contamination. Examples of such devices include syringe plunger rods of a three-piece syringe, needle shields, safety shields of injection devices and the finger flanges of a syringe barrel, handle of peripheral IV catheter, catheter wings, catheter flow control plug etc. Medical devices and components formed from recycled resin compositions may also be characterized as fluid path contact medical devices. Such medical devices or medical device components may include syringe barrels, needle hubs, surgical blade handles, valve housings, syringe stopper, plunger rod of a two piece syringe.

Figure 2:
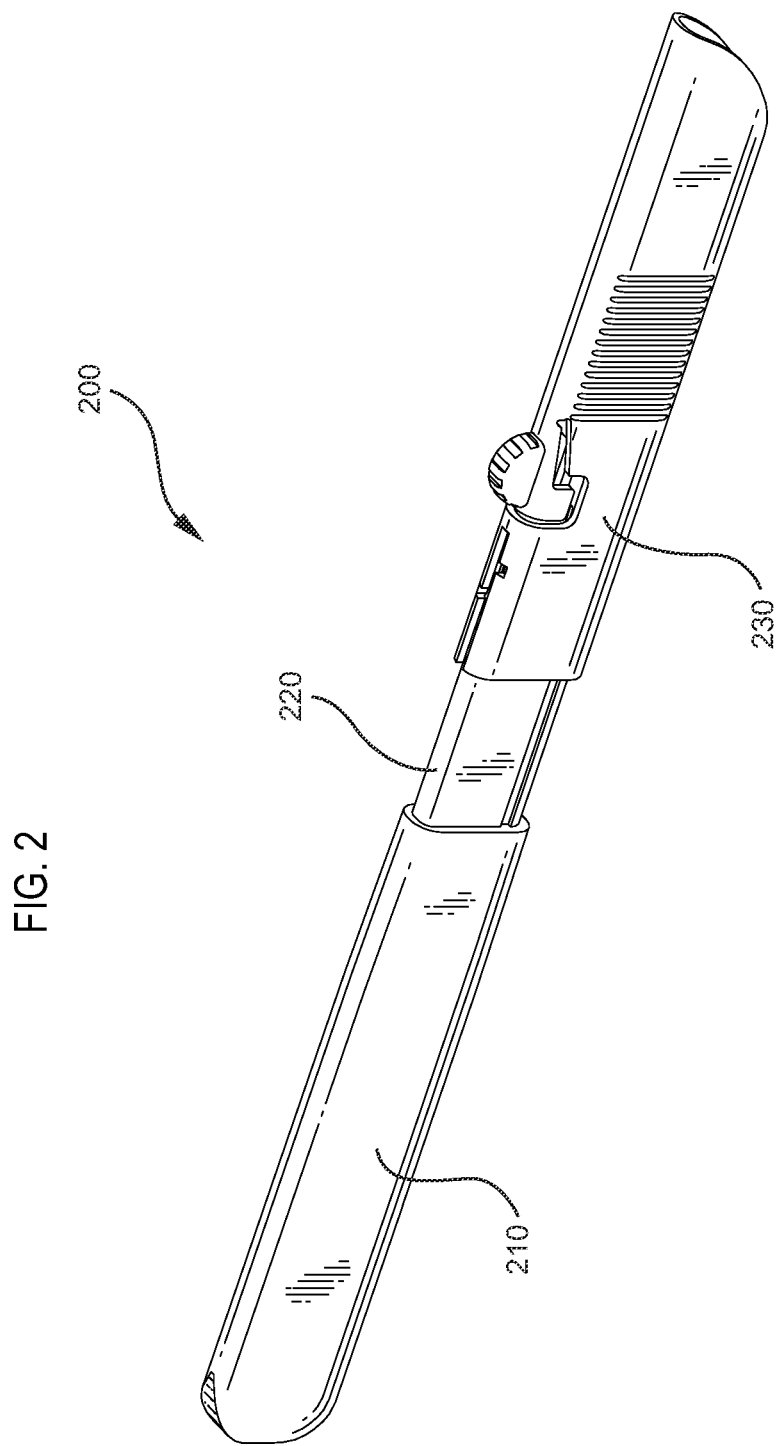
FIG. 2 illustrates a perspective view of a scalpel and scalpel shield according to one or more embodiments.

Non-limiting examples of medical devices are illustrated in FIGS. 1 and 2. FIG. 1 illustrates a syringe assembly 100 including a syringe barrel 110 with an inside surface defining a chamber, a plunger rod 120 disposed within the chamber, a needle hub 130 including a needle cannula 140 for attachment to the syringe barrel. FIG. 1 also illustrates an optional needle shield 150 to be attached to the needle hub 130 to protect and cover the needle cannula 140. The plunger rod 120 has an elongate body 121 extending between a proximal end 122 and a distal end 123 which define the length of the elongate body 121. The plunger rod has a thumbpress 124 positioned at the proximal end 122 of the elongate body 121 and a stopper support 126 positioned at the distal end 123 of the elongate body 121. The stopper support 126 can be any suitable structure for supporting a stopper 125. The plunger rod 120 may include a separate stopper 125 attached to one end of the plunger rod 120 for forming a fluid tight seal with the inside surface of the syringe barrel, as shown in FIG. 1. In one or more alternative embodiments, the plunger rod 120 may include a sealing portion (not shown) that functions as a stopper, and may be integrally molded with the plunger rod 120 and thus formed form the same material as the plunger rod 120. The syringe barrel 110 shown in FIG. 1 also includes a luer fitting 112 at one end of the syringe barrel 110 and a finger flange 114 at the opposite end of the syringe barrel 110.

In one variant, the syringe barrel may be entirely formed from the recycled resin compositions disclosed herein. Alternatively, the luer fitting 112 and/or the finger flanges 114 may be formed from the recycled resin compositions disclosed herein, while the syringe barrel 110 is formed from known resin compositions that may include virgin resin components and/or biobased resin components, and are free of any recycled resin. In one or more alternative configurations, the inside surface of the syringe barrel 110 may be coated with known a resin composition(s) that may include virgin resin components and/or biobased resin components, and are free of any recycled resin, while the remainder of the syringe barrel 110 is formed form one or more of the recycled resin compositions described herein.

In one variant, the plunger rod 120 may be formed from the recycled resin compositions described herein. In embodiments which incorporate a sealing edge (not shown) into the plunger rod 120, the sealing edge (not shown) may also be formed from the recycled resin compositions described herein. In one or more embodiments, the stopper 125 may be formed from elastomeric or other known materials, while the plunger rod is formed from the recycled resin compositions and is attached to the stopper 125.

In one or more embodiments, the needle hub 130 may be formed from the recycled resin compositions described herein, while the needle cannula 140 is made from known materials in the art. In one or more alternative configurations, the needle shield 150 may also be formed from the recycled resin compositions disclosed herein.

FIG. 2 illustrates a scalpel 200 that includes an elongate handle 210 and blade holder 220 for attaching a blade (not shown) to the elongate handle. The scalpel 200 also includes a blade shield 230 that is removably attached to the elongate handle 210 and/or the blade holder 220 to protect the blade (not shown). In one or more embodiments, the elongate handle 210, blade holder 220 and/or the blade shield 230 may be formed from the recycled resin compositions described herein.

FIGS. 3A through 3E show various view of an embodiment of the invention. Referring to FIG. 3A the elongate body 121 is cylindrical and there are a plurality of openings 160 therethrough. The plurality of openings 160 are spaced along the length of the elongate body 121. The openings decrease the weight of the plunger rod and the amount of material required to construct the plunger rod. The openings 160 can be formed by any suitable method including, but not limited to, drilling and as part of a mold. FIG. 3B shows a side view of the plunger rod in FIG. 3A. FIG. 3C shows a top view of the plunger rod of FIG. 3A. FIGS. 3D and 3E show views from the proximal end and distal end, respectively. While the plurality of openings 160 are shown circular, it will be understood by those skilled in the art that the openings can be any suitable shape. Examples of various shapes are shown throughout the figures. None of these examples should be taken as limiting the scope of the invention.

With reference to FIGS. 4A-4F, some embodiments of the syringe plunger rod have an elongate body 121 comprising at least one rib 165 extending the length of the elongate body 121. At least one of the at least one ribs 165 comprises a plurality of spaced apart openings 160. FIGS. 4A-4F show another embodiment of a syringe plunger rod having four ribs 165, two of which have a plurality of openings 160. FIGS. 4A through 4E show, respectively, a perspective view, a side view, a top view, a view from the proximal end and a view from the distal end of the plunger rod. The four ribs 165 are arranged so that the cross-section (shown in FIG. 4F) is plus-shaped. In various embodiments, all four ribs 165 have openings 160, or three ribs 165 have openings 160, or only one rib 165 has openings 160. In detailed embodiments, at least one of the ribs 165, but less than all of the ribs 165 have openings 160.

Figure 4A:
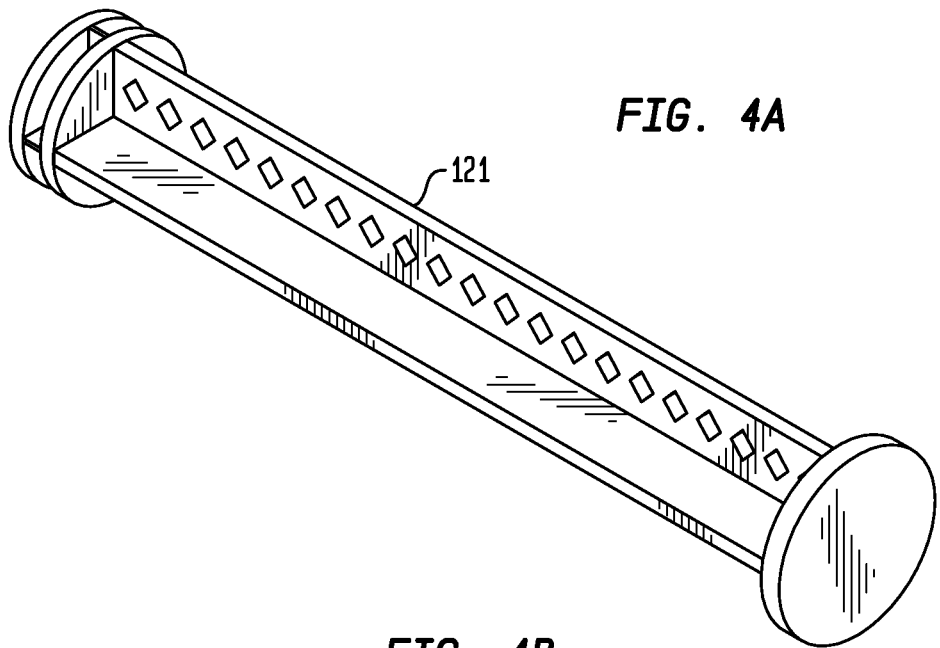
FIGS. 4A-4F illustrate a syringe plunger rod according to one or more embodiment of the invention.
Figure 4B:
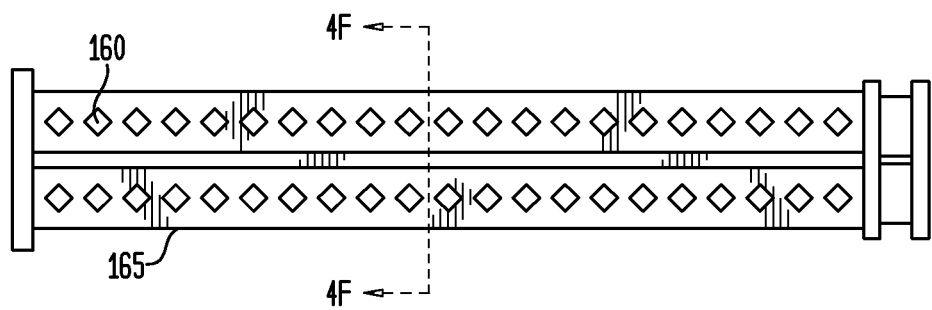
Figure 4C:
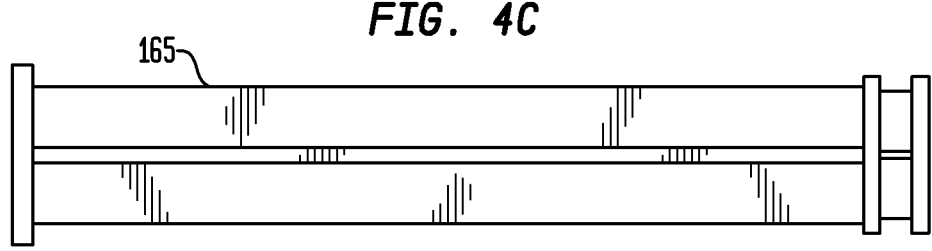
Figure 4D:
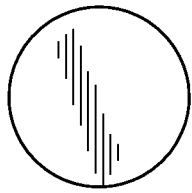
Figure 4E:
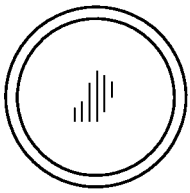
Figure 4F:
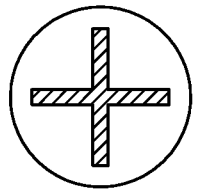

In some embodiments, as that shown in FIG. 4A, the elongate body comprises at least two ribs extending the length of the elongate body and the plurality of spaced openings are positioned along the length of less than all of the ribs. Referring to FIG. 4A, the elongate body has four ribs extending the length of the body but the openings are present only along two of the four ribs. Therefore, the openings are on less than all of the ribs. The number of ribs and ribs with openings discussed here is merely exemplary and should not be taken as limiting the scope of the invention.

Figure 5A:
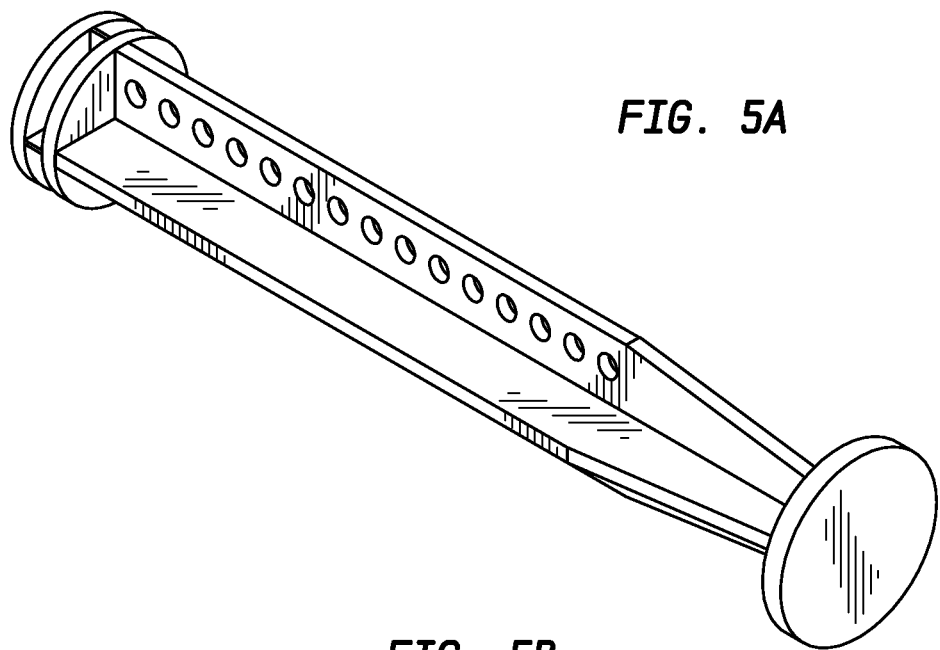
FIGS. 5A-5F illustrate a syringe plunger rod according to one or more embodiment of the invention.
Figure 5B:
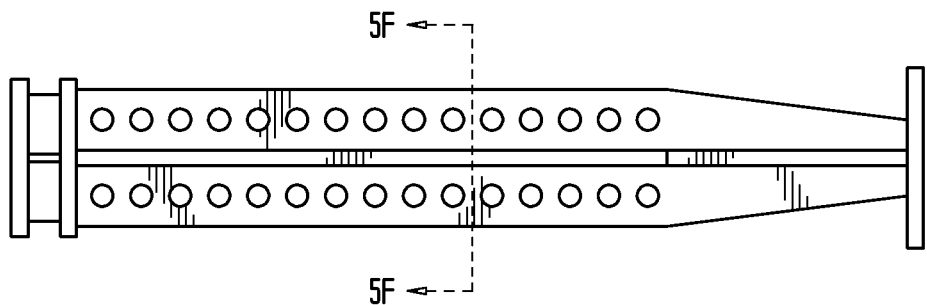
Figure 5C:
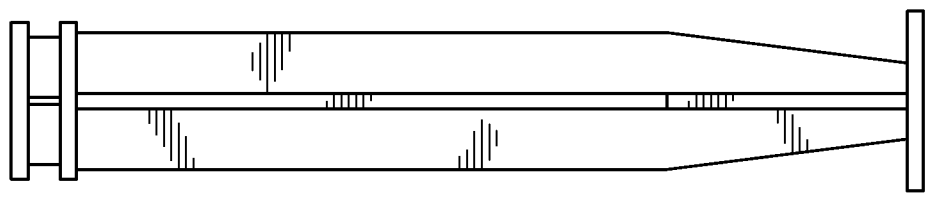
Figure 5D:
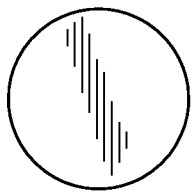
Figure 5E:
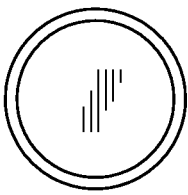
Figure 5F:
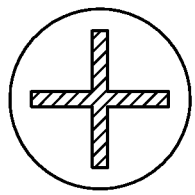

FIG. 5A shows another embodiment of a syringe plunger rod having four ribs. Two of the ribs are shown with a plurality of spaced openings, but it will be understood that any or all of the ribs can have openings. FIGS. 5A through 5E show, respectively, a perspective view, a side view, a top view, a view from the proximal end and a view from the distal end of the plunger rod. FIG. 5F shows a cross sectional view of the ribs with the plug shape configuration illustrated.

FIG. 6A shows another embodiment of a syringe plunger rod having four ribs. Two of the ribs are shown with a plurality of spaced openings, but it will be understood that any or all of the ribs can have openings. FIGS. 6A through 6E show, respectively, a perspective view, a side view, a top view, a view from the proximal end and a view from the distal end of the plunger rod. FIG. 6F shows a cross sectional view of the ribs with the plug shape configuration illustrated.

Figure 7A:
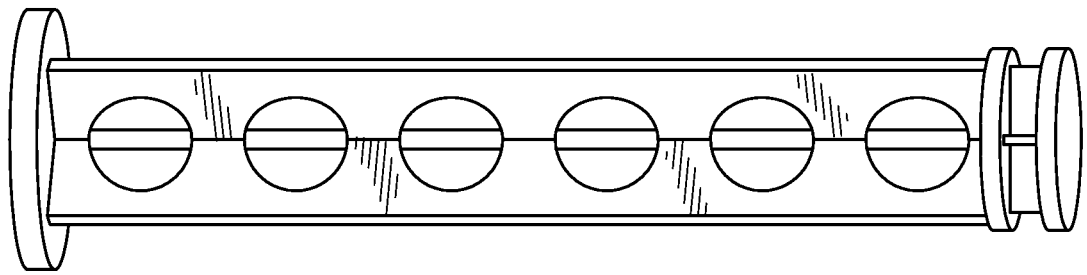
FIGS. 7A-7F illustrate a syringe plunger rod according to one or more embodiment of the invention.
Figure 7B:
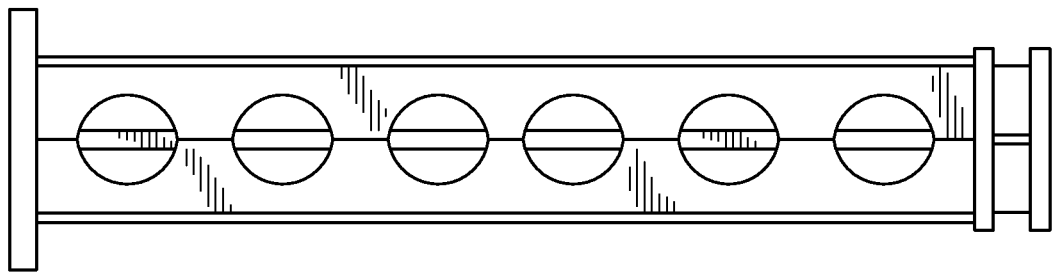
Figure 7C:
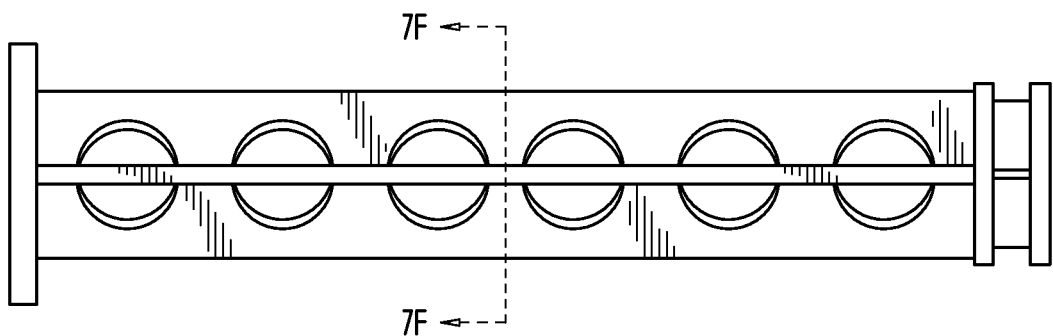
Figure 7D:
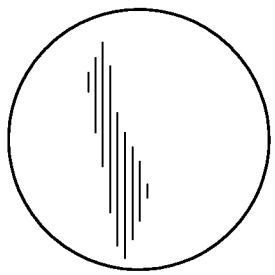
Figure 7E:
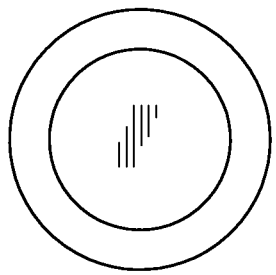
Figure 7F:
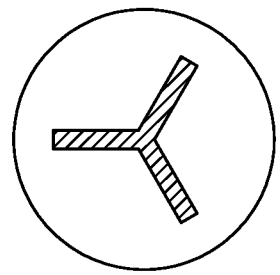

In some embodiments, the elongate body comprises three ribs. This can be seen, for example, in FIGS. 7A through 7F. In FIGS. 7A-7F, the plurality of spaced openings are present on all of the ribs. However, it will be understood that the openings can be located on any or all of the ribs and can have any shape. In detailed embodiments, the plurality of spaced apart openings are positioned along two of the three ribs. In specific embodiments, the plurality of spaced apart openings are positioned on one of the three ribs. FIGS. 7A through 7E show, respectively, a perspective view, a side view, a top view, a view from the proximal end and a view from the distal end of the plunger rod. FIG. 7F shows a cross sectional view of an elongate body with three ribs. In some embodiments, as shown in FIG. 7A-7C, the spaced openings have a spherical shape with its center at an intersection of at least two of the ribs.

FIGS. 8A through 8F show another embodiment of the invention in which a plurality of support walls 168 are spaced along the length of the elongate body 121. In the embodiment shown, the three ribs have a plurality of openings throughout each rib. The openings are relatively large, leaving relatively little material on the ribs. The support walls 168 may be dispersed in any or all of the openings to provide additional support to the plunger rod. FIGS. 8A through 8E show, respectively, a perspective view, a side view, a top view, a view from the proximal end and a view from the distal end of the plunger rod. FIG. 8F shows a cross sectional view of an elongate body with three ribs and support walls.

Figure 9A:
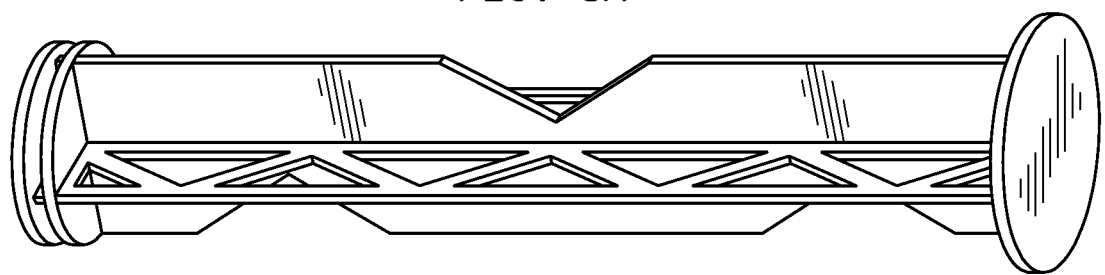
FIGS. 9A-9F illustrate a syringe plunger rod according to one or more embodiment of the invention.
Figure 9B:
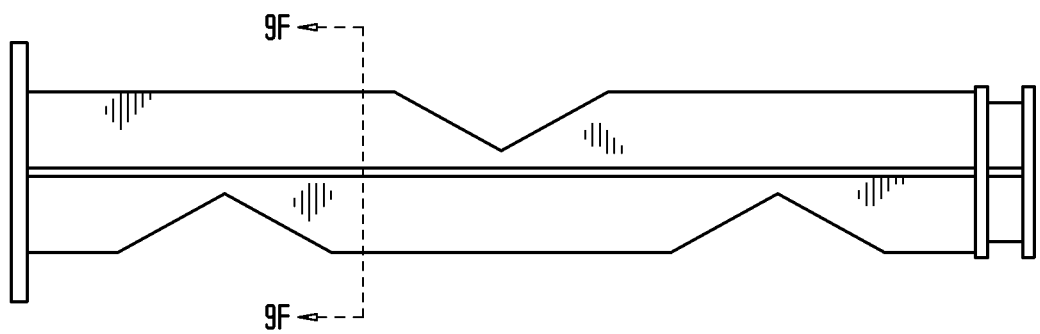
Figure 9C:
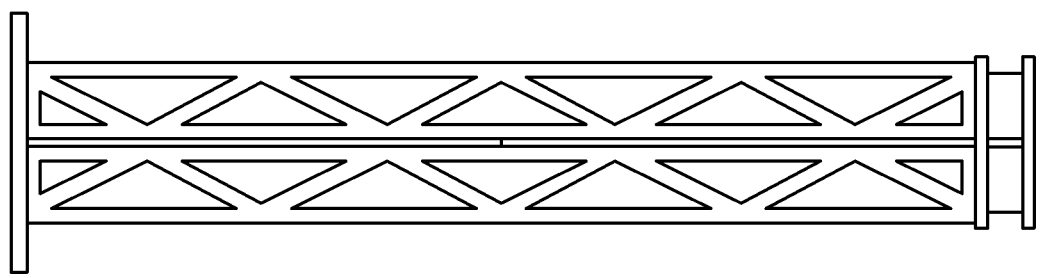
Figure 9D:
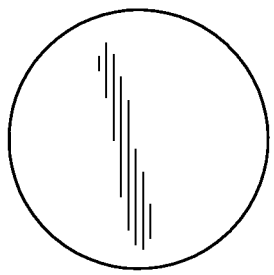
Figure 9E:
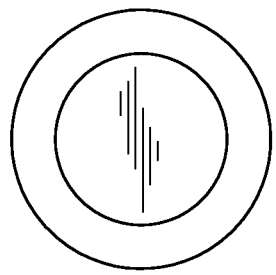
Figure 9F:
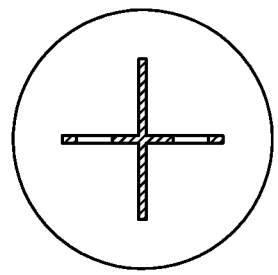

FIG. 9A shows another embodiment of the invention in which the plunger rod has four ribs in a plus shape. In this embodiment, some of the ribs have different shapes including notches. The notches may serve to reduce the amount of material used in the construction of the plunger rod without significantly impacting the usefulness of the plunger rod. FIGS. 9A through 9E show, respectively, a perspective view, a side view, a top view, a view from the proximal end and a view from the distal end of the plunger rod. FIG. 9F shows a cross sectional view of an elongate body with four ribs.

Figure 10A:
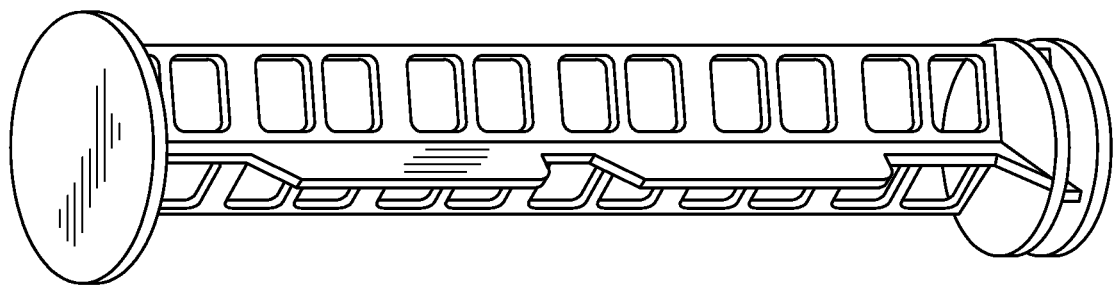
FIGS. 10A-10F illustrate a syringe plunger rod according to one or more embodiment of the invention.
Figure 10B:
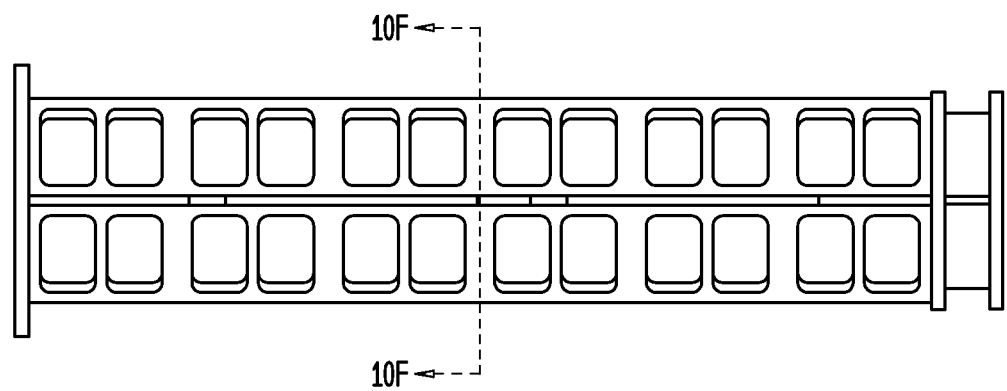
Figure 10C:
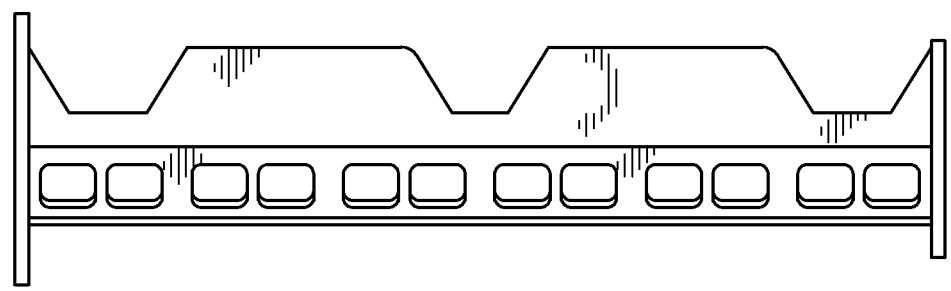
Figure 10D:
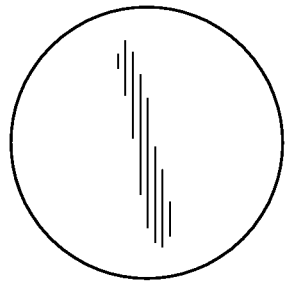
Figure 10E:
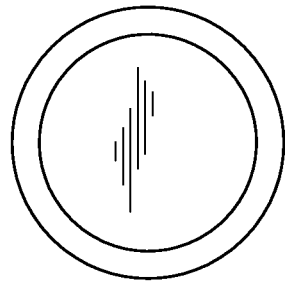
Figure 10F:
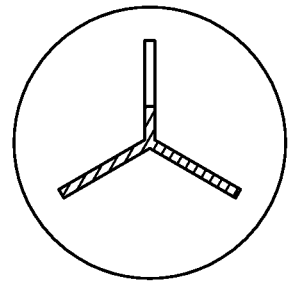

FIG. 10A shows another embodiment of the invention in which the plunger rod has three ribs. In this embodiment, some of the ribs have different shapes including notches. FIGS. 10A through 10E show, respectively, a perspective view, a side view, a top view, a view from the proximal end and a view from the distal end of the plunger rod. FIG. 10F shows a cross sectional view of an elongate body with three ribs.

Figure 11A:
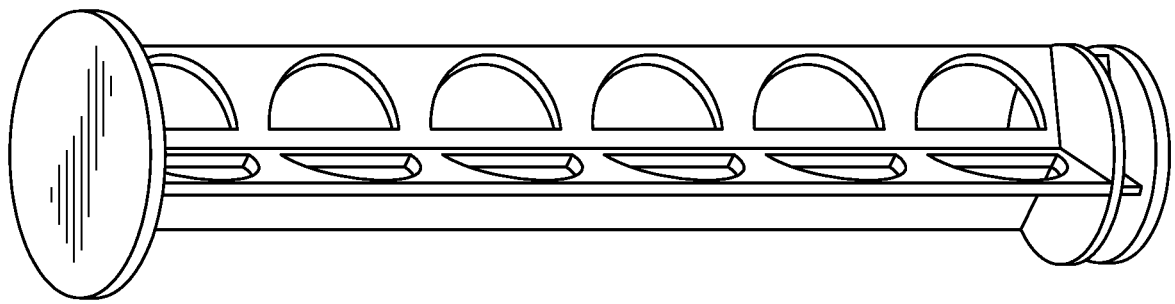
FIGS. 11A-11F illustrate a syringe plunger rod according to one or more embodiment of the invention.
Figure 11B:
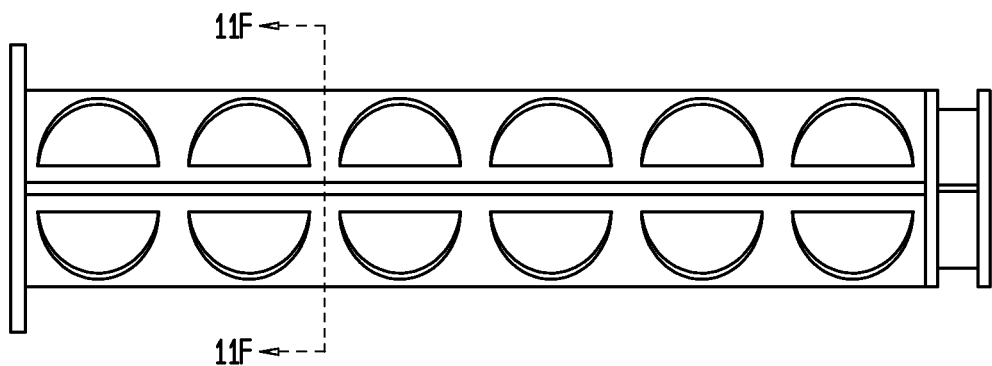
Figure 11C:
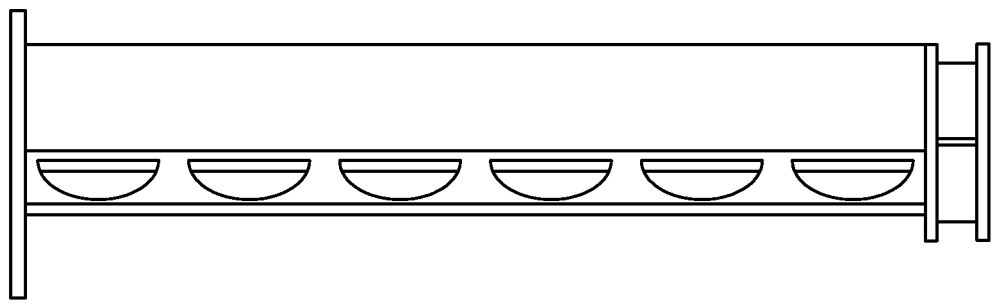
Figure 11D:
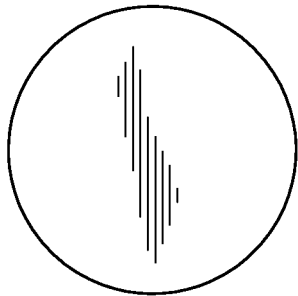
Figure 11E:
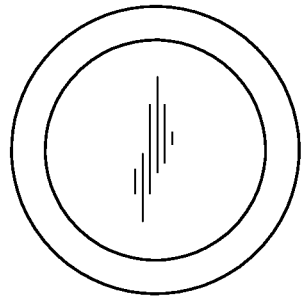
Figure 11F:
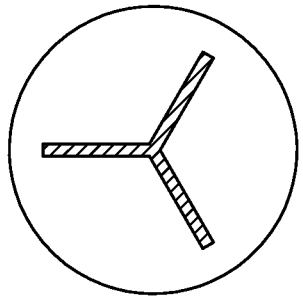

FIG. 11A shows another embodiment of the invention in which the plunger rod has three ribs and the plurality of openings are half-moon shaped. FIGS. 11A through 11E show, respectively, a perspective view, a side view, a top view, a view from the proximal end and a view from the distal end of the plunger rod. FIG. 11F shows a cross sectional view of the elongate body with three ribs.

Figure 12A:
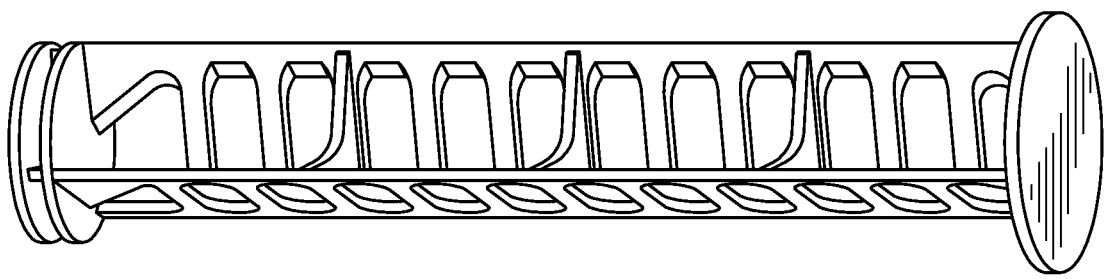
Figure 12B:
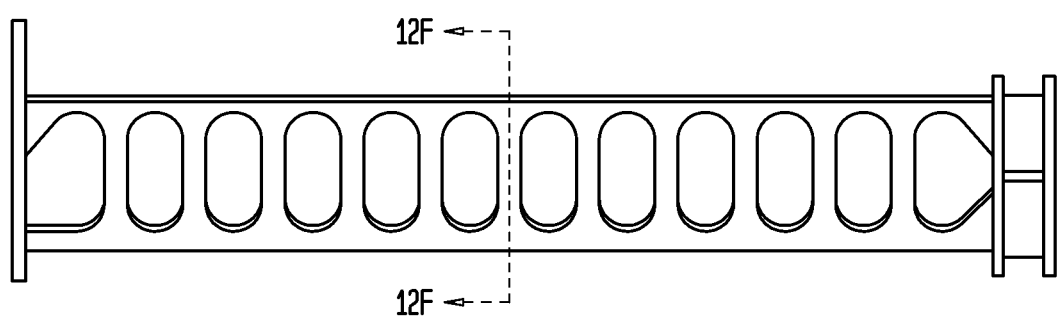
Figure 12C:
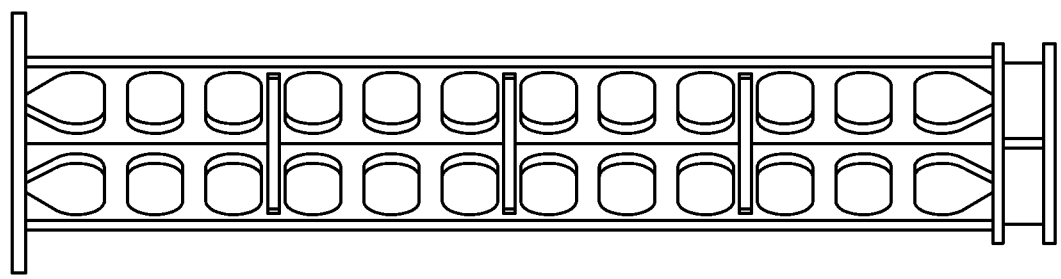
Figure 12C:
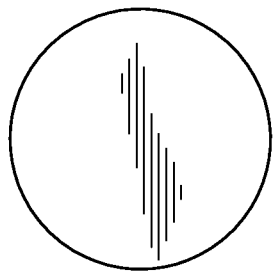
Figure 12C:
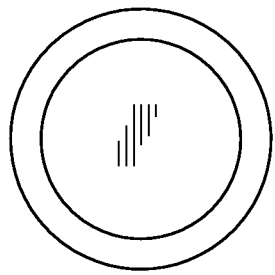
Figure 12C:
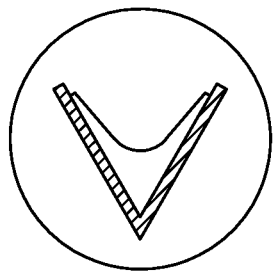

FIG. 12A shows another embodiment of the invention in which the plunger rod has two ribs in a v-shape. To strengthen this configuration, it may be useful to include a plurality of support walls spaced along the length of the elongate body. FIGS. 12A through 12E show, respectively, a perspective view, a side view, a top view, a view from the proximal end and a view from the distal end of the plunger rod. FIG. 12F shows a cross sectional view of the elongate body with two ribs and support walls.

FIG. 13A shows another embodiment of the invention in which the plunger rod has four ribs in plus-sign shape with two additional ribs along one elongate axis, one above the main cross rib and one below the main cross rib. FIGS. 13A through 13E show, respectively, a perspective view, a side view, a top view, a view from the proximal end and a view from the distal end of the plunger rod. FIG. 12F shows a cross sectional view of the elongate body showing the four main ribs in the plus-sign shape with the two additional ribs shown above and below the horizontal main cross rib.

Figure 14A:
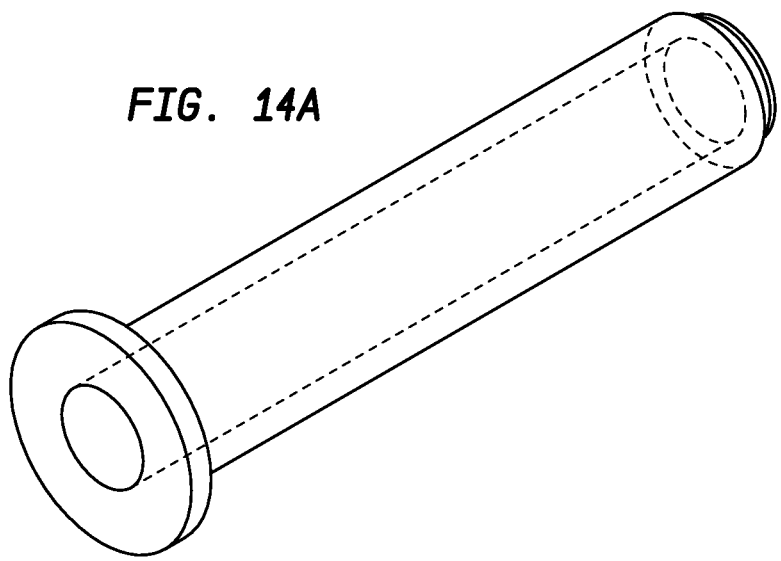
FIGS. 14A-14F illustrate a syringe plunger rod according to one or more embodiment of the invention.
Figure 14B:
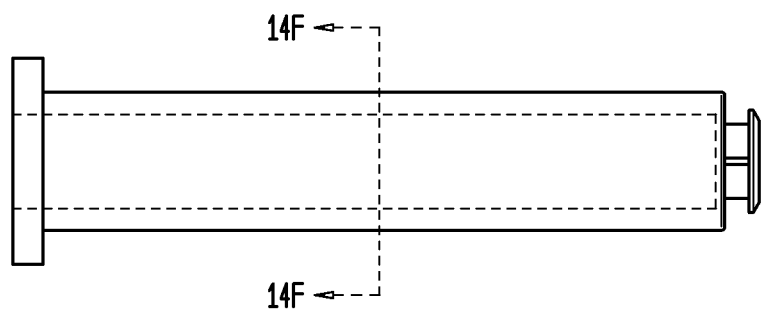
Figure 14C:
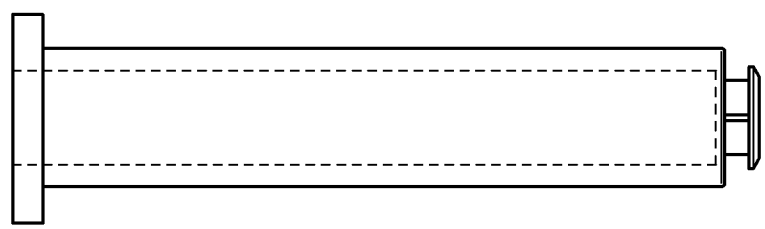
Figure 14D:
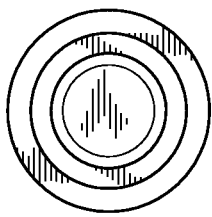
Figure 14E:
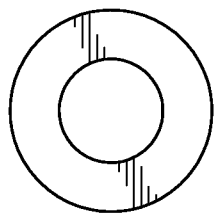
Figure 14F:
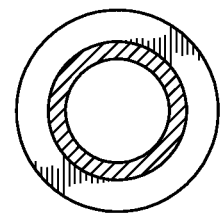

FIG. 14A shows another embodiment of the invention in which the plunger rod has an elongate cylindrical hollow form with a hollow portion therein and a thumbpress on the proximal end. The thumbpress can have an opening aligned with the elongate hollow form or can be solid, enclosing the hollow portion of the elongate cylindrical body. The elongate cylindrical hollow form can be open-ended, closed at one end (either proximal or distal) or closed at both ends. The closures can be integrally formed, or can be a separate piece attached to the hollow cylinder. The walls of the elongate cylindrical hollow body can have any suitable thickness providing sufficient strength to withstand pushing the plunger rod through a syringe barrel. A thicker wall with have more strength but require additional material to manufacture. FIGS. 14A through 14E show, respectively, a perspective view, a side view, a top view, a view from the proximal end and a view from the distal end of the plunger rod. FIG. 14F shows a cross sectional view of the elongate cylindrical hollow body.

The shape of the elongate cylindrical hollow body and the hollow portion can vary. In specific embodiments, the shape of the hollow portion is similar to that of the elongate body. For example, the elongate body can be round and the hollow portion can be round matching the shape of the elongate body. In various embodiments, the elongate body is square, rectangular or octagonal and the hollow portion is square, rectangular or octagonal, respectively. Additionally, the shape of the hollow portion can be different from that of the elongate body. For example, a square elongate body may have a round hollow portion extending along the length of the elongate body.

Figure 15A:
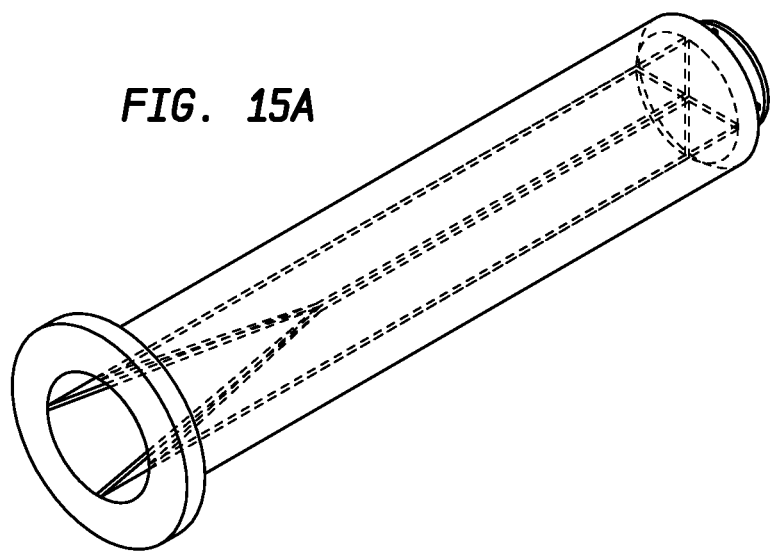
FIGS. 15A-15F illustrate a syringe plunger rod according to one or more embodiment of the invention.
Figure 15B:
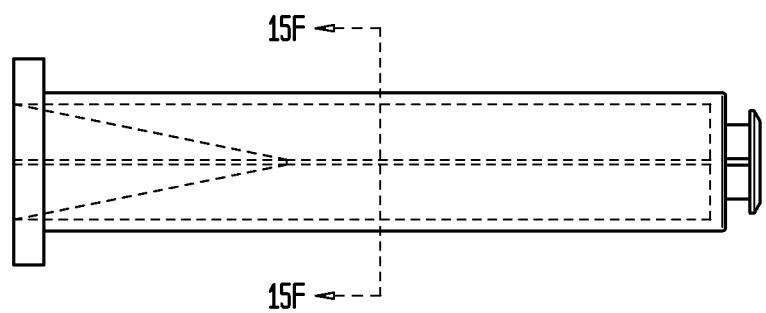
Figure 15C:
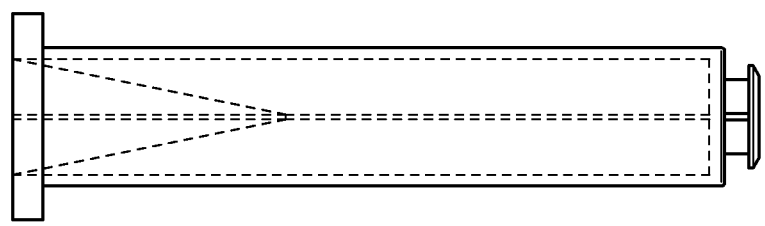
Figure 15D:
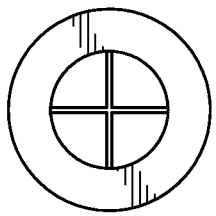
Figure 15E:
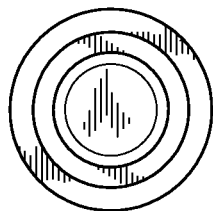
Figure 15F:
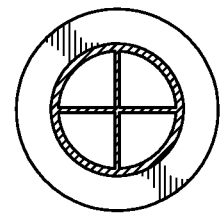
Figure 16A:
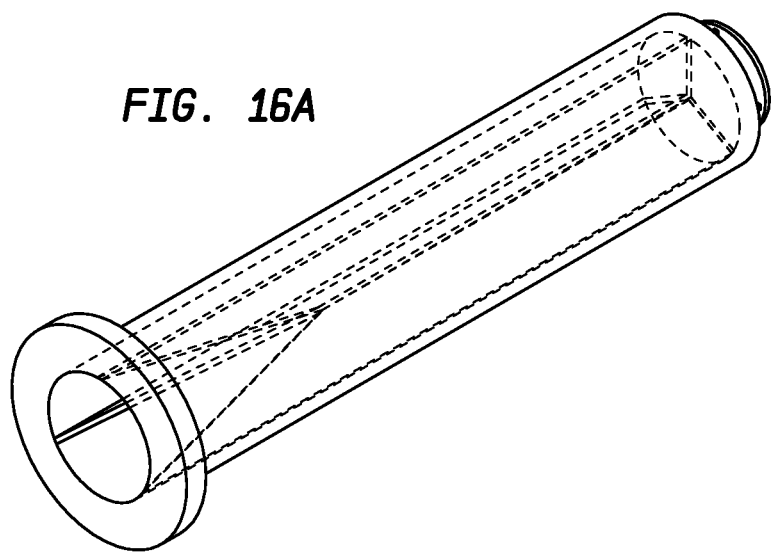
FIGS. 16A-16F illustrate a syringe plunger rod according to one or more embodiment of the invention.
Figure 16B:
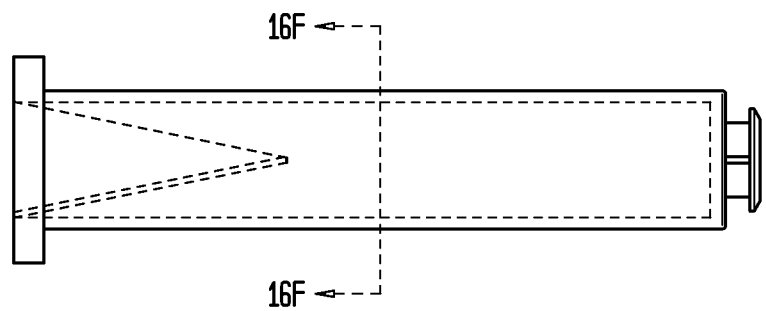
Figure 16C:
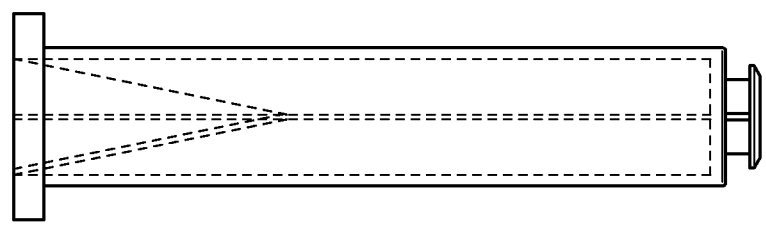
Figure 16D:
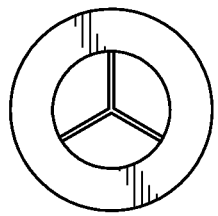
Figure 16E:
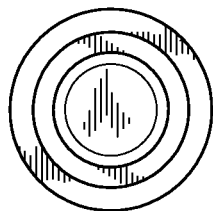
Figure 16F:
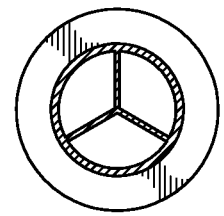
Figure 19:
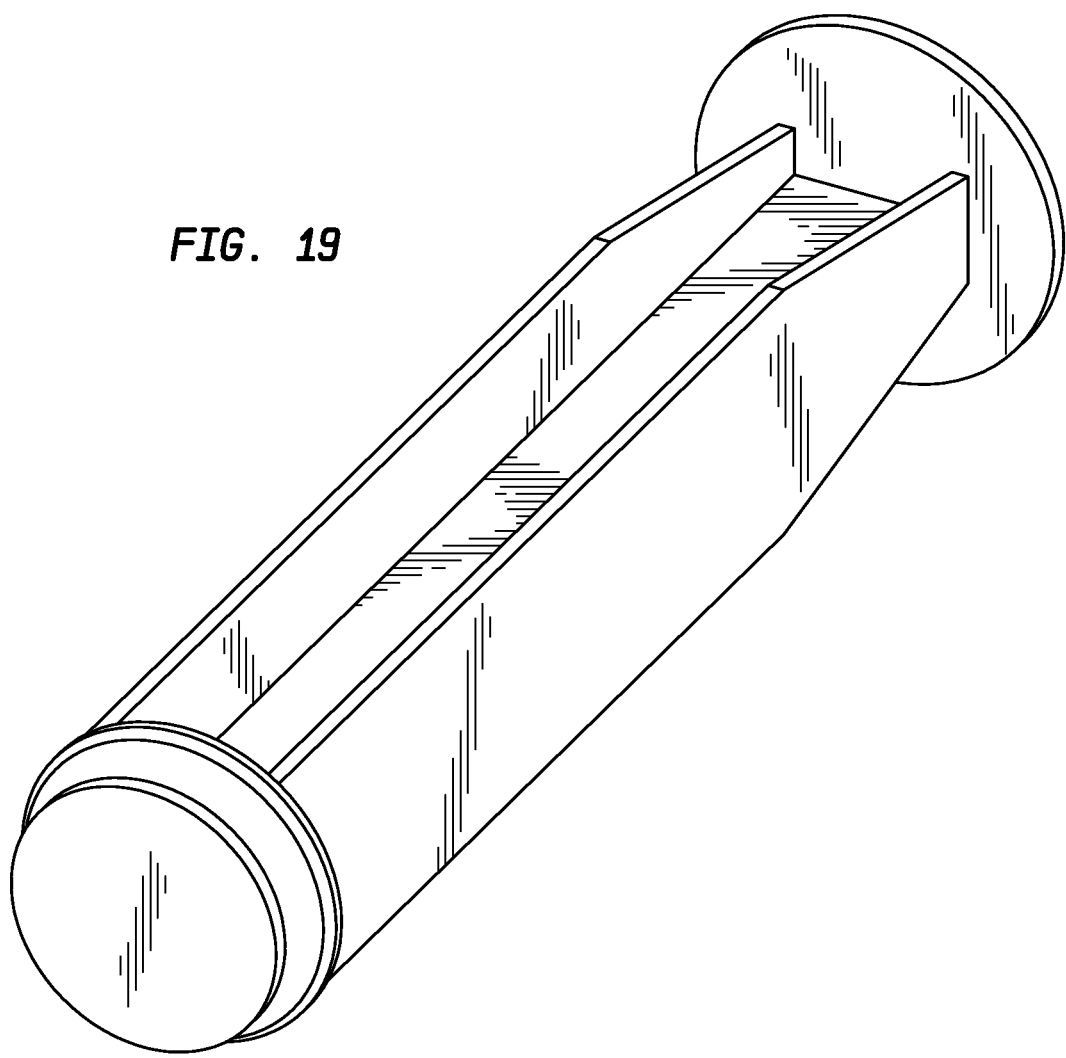
FIG. 19 illustrates a syringe plunger rod according to one or more embodiment of the invention.
Figure 20:
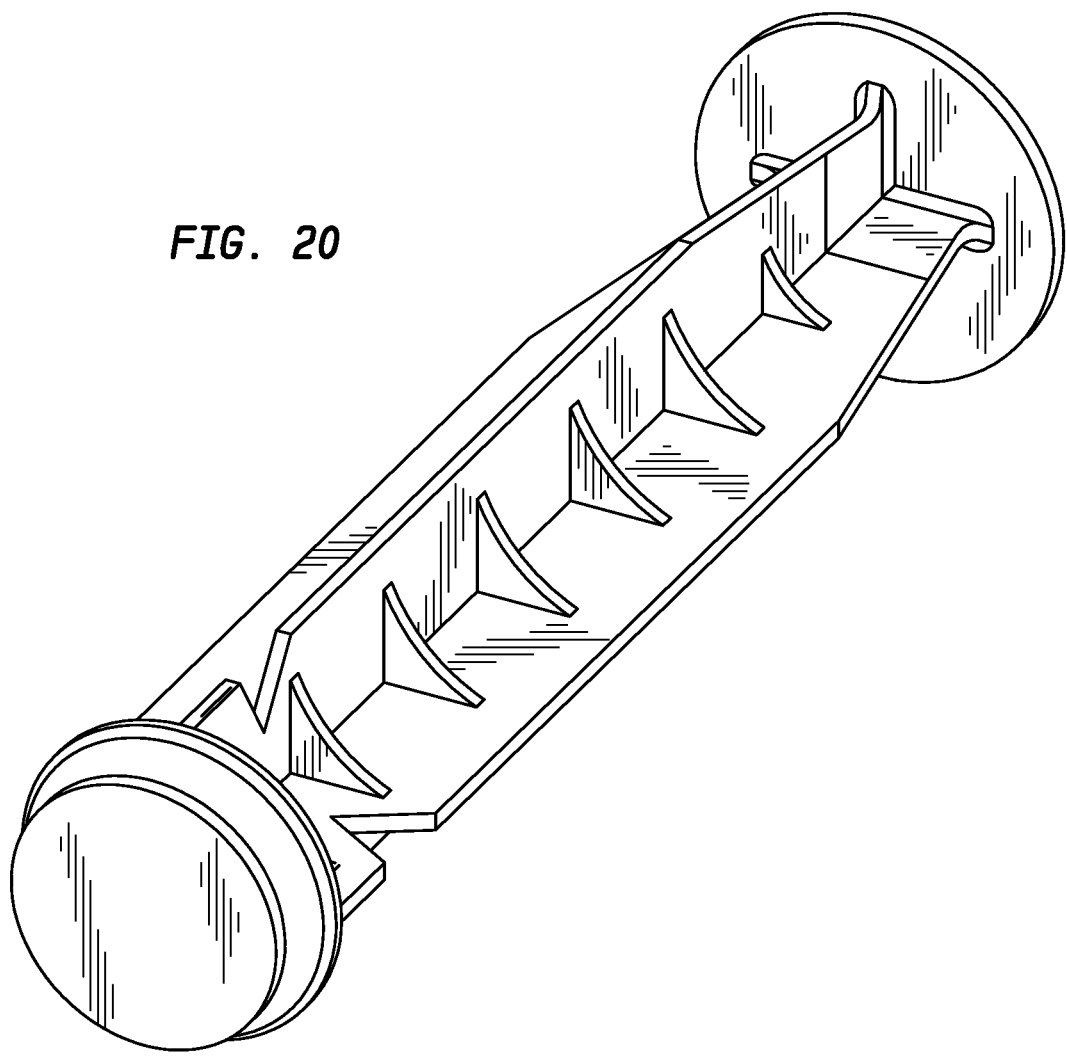
FIG. 20 illustrates a syringe plunger rod according to one or more embodiment of the invention.
Figure 21:
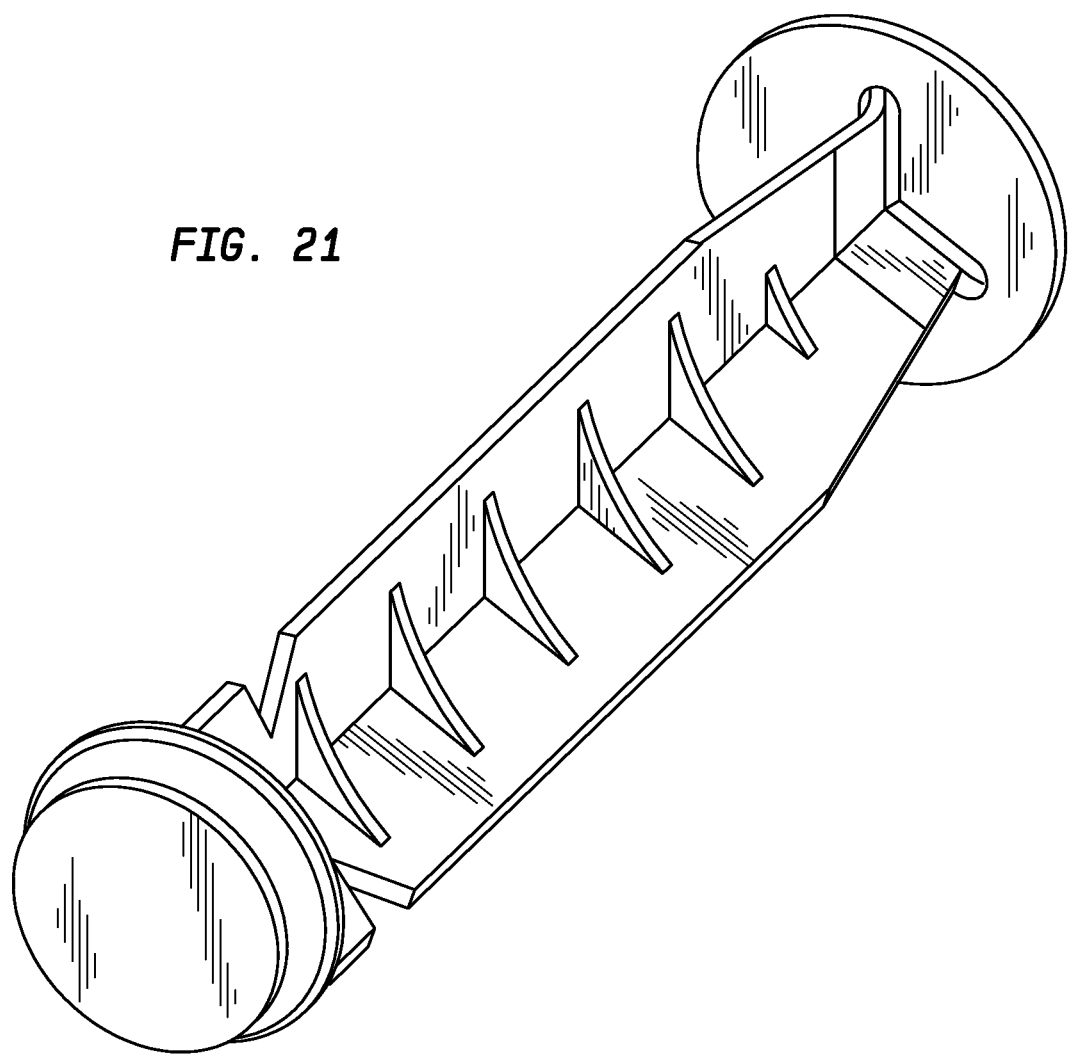
FIG. 21 illustrates a syringe plunger rod according to one or more embodiment of the invention.
Figure 22A:
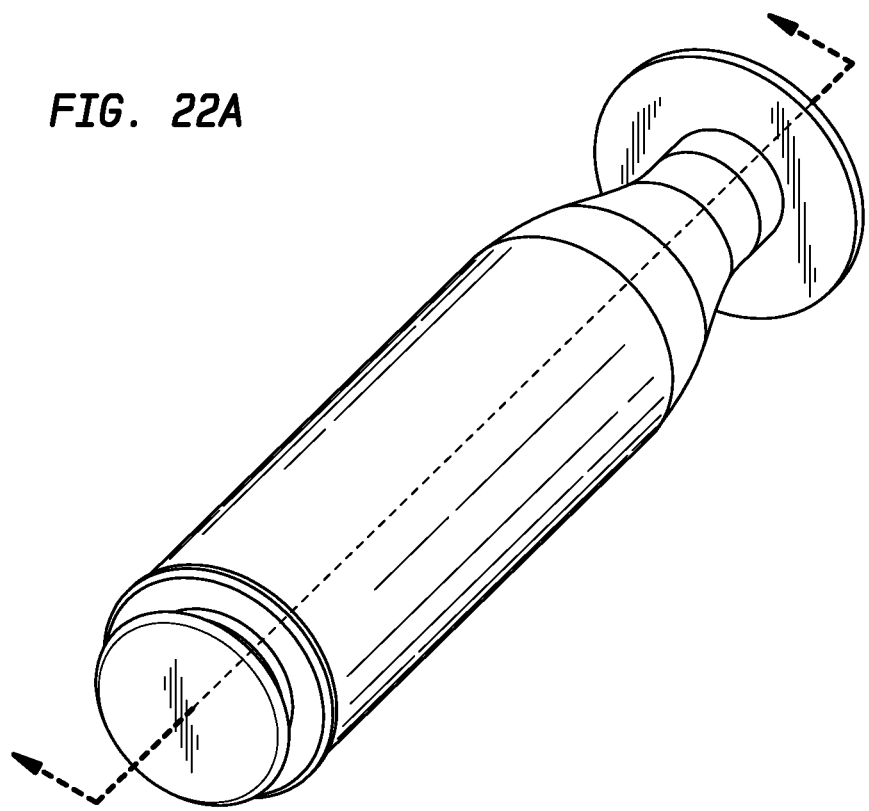
FIG. 22A illustrates a syringe plunger rod according to one or more embodiment of the invention.
Figure 22B:
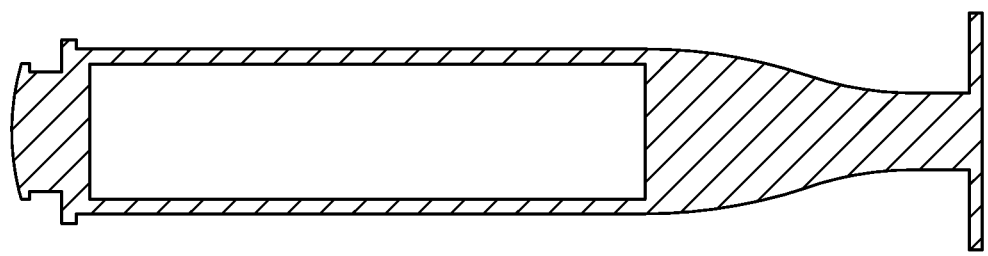
FIG. 22B illustrates a cross-section of the syringe plunger rod of FIG. 22A.

FIG. 15A shows another embodiment of the invention in which the plunger rod has a hollow shape similar to that of FIG. 14A. In FIGS. 15A through 15F, the hollow plunger rod has a combination of ribs extending axially along the length of the cylindrical hollow body. The ribs are shown in a plus-shaped configuration. The ribs can extend the entire length of the body or can be along a partial length. In the embodiment shown, the rigs extend from the stopper end of the plunger rod to a point about ⅔ of the length of the plunger rod. At that point, the ribs taper toward the inside of the hollow plunger rod. Those skilled in the art will understand that this is merely illustrative of one particular embodiment and that the length of the ribs extending along plunger rod can vary. Additionally, the end of the ribs can be blunt or tapered as shown. The taper can have any shape and length as desired.

FIGS. 16A through 16F show a similar configuration with three ribs extending along the length of the hollow cylindrical body. FIGS. 17A through 17F show a similar configuration in which the body of the elongate barrel is square shaped. FIGS. 18A through 18F show a similar configuration in which the body of the elongate barrel is an elongate octagon shape. It will be understood by those skilled in the art that the cross-sectional shape of the elongate hollow body can be any suitable shape including, but not limited to, triangle, pentagon, hexagon, heptagon, nonagon and decagon shaped.

FIGS. 19 through 29 show various embodiments of the invention. The plunger rods may be cylindrical or made of a plurality of ribs and may have support walls. The embodiments shown are merely illustrative and should not be taken as limiting the scope of the invention. FIG. 22A shows an elongate body with a hollow portion in which the hollow portion is enclosed within the elongate body. This is shown best in the cross-section of FIG. 22B. Here, the hollow portion is completely contained within the elongate body, but it will be understood that the hollow portion may extending to one or both of the ends of the elongate body.

Figure 23A:
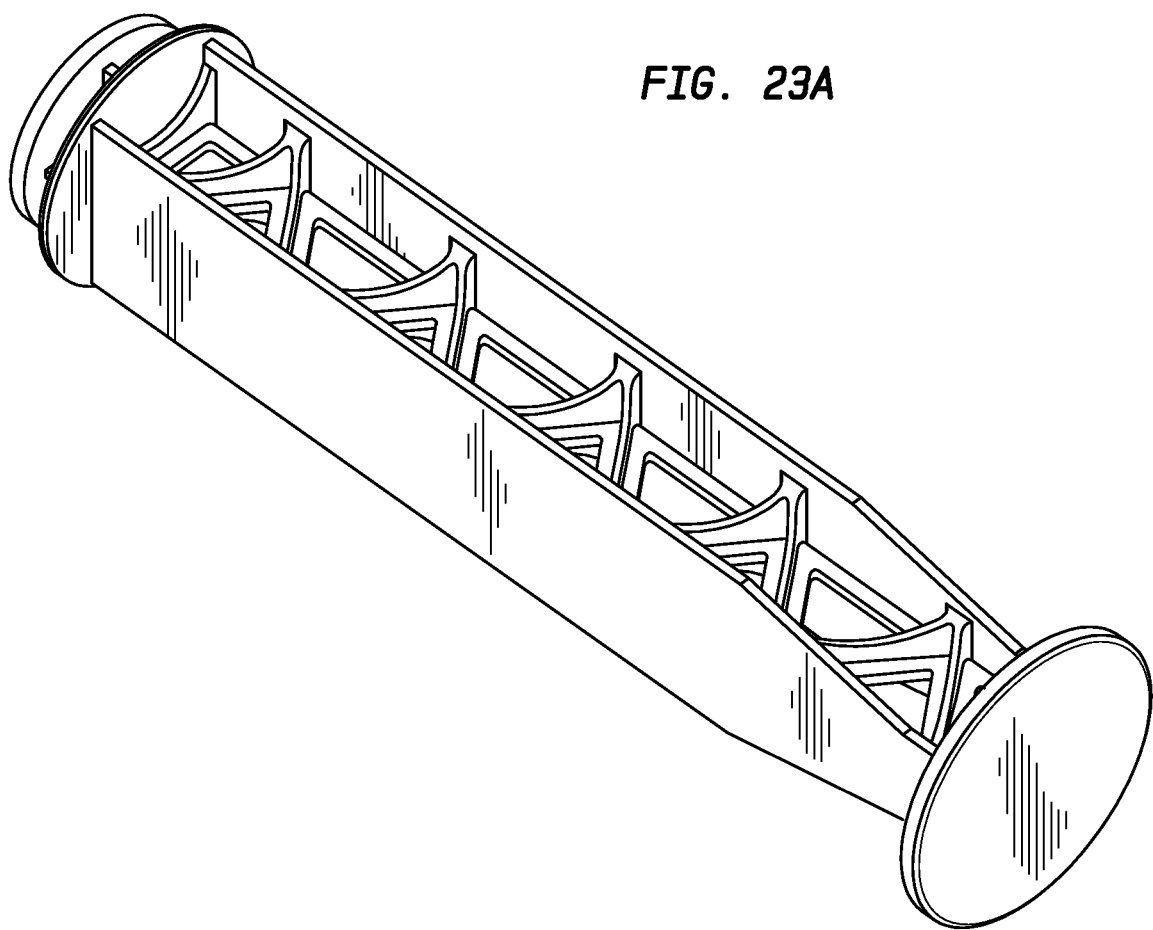
FIGS. 23A-23F illustrate a syringe plunger rod according to one or more embodiment of the invention.
Figure 23B:
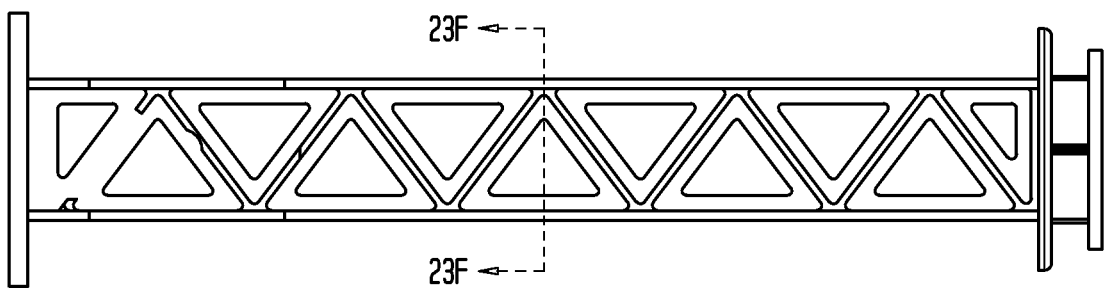
Figure 23C:
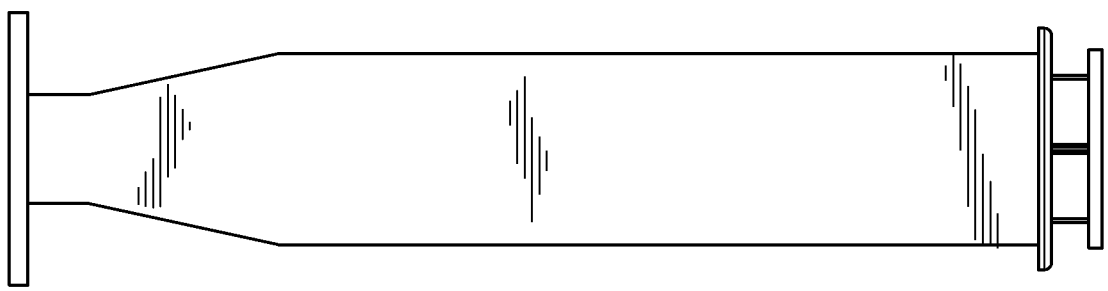
Figure 23D:
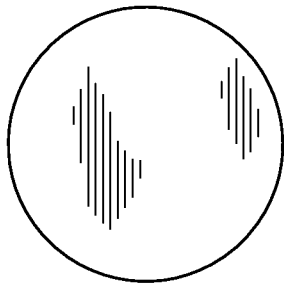
Figure 23E:
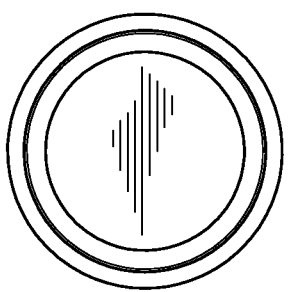
Figure 23F:
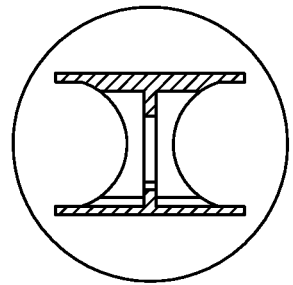
Figure 24:
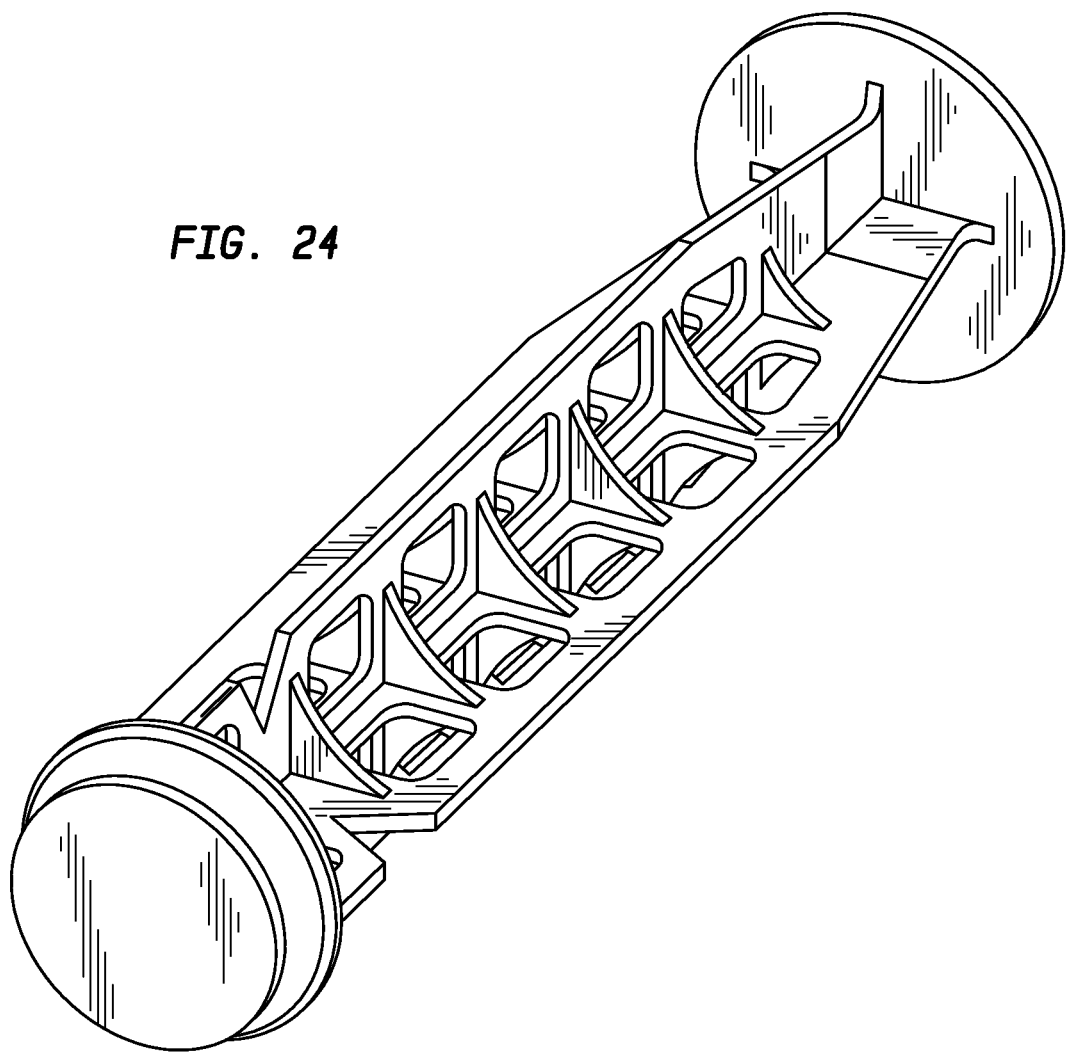
FIG. 24 illustrates a syringe plunger rod according to one or more embodiment of the invention.
Figure 25:
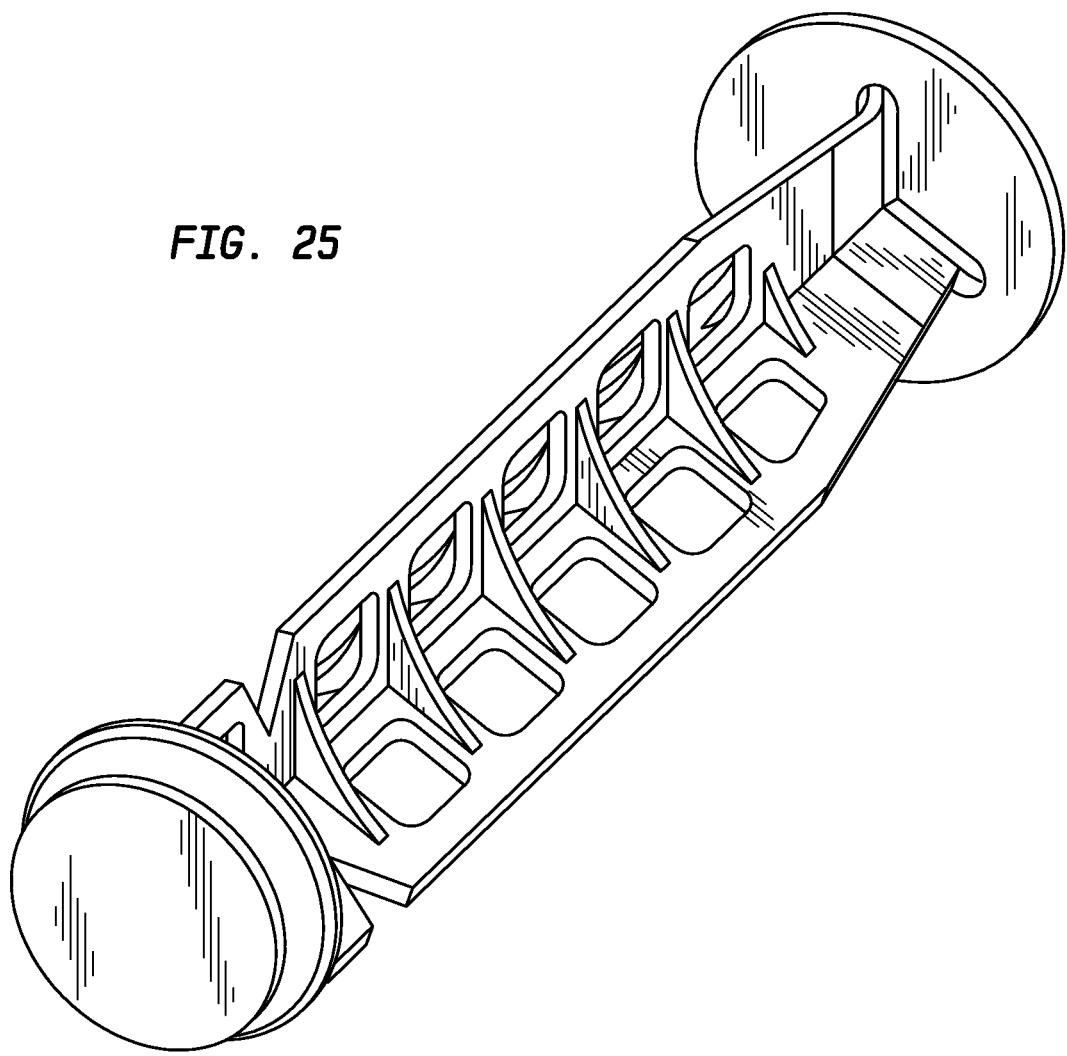
FIG. 25 illustrates a syringe plunger rod according to one or more embodiment of the invention.
Figure 27:
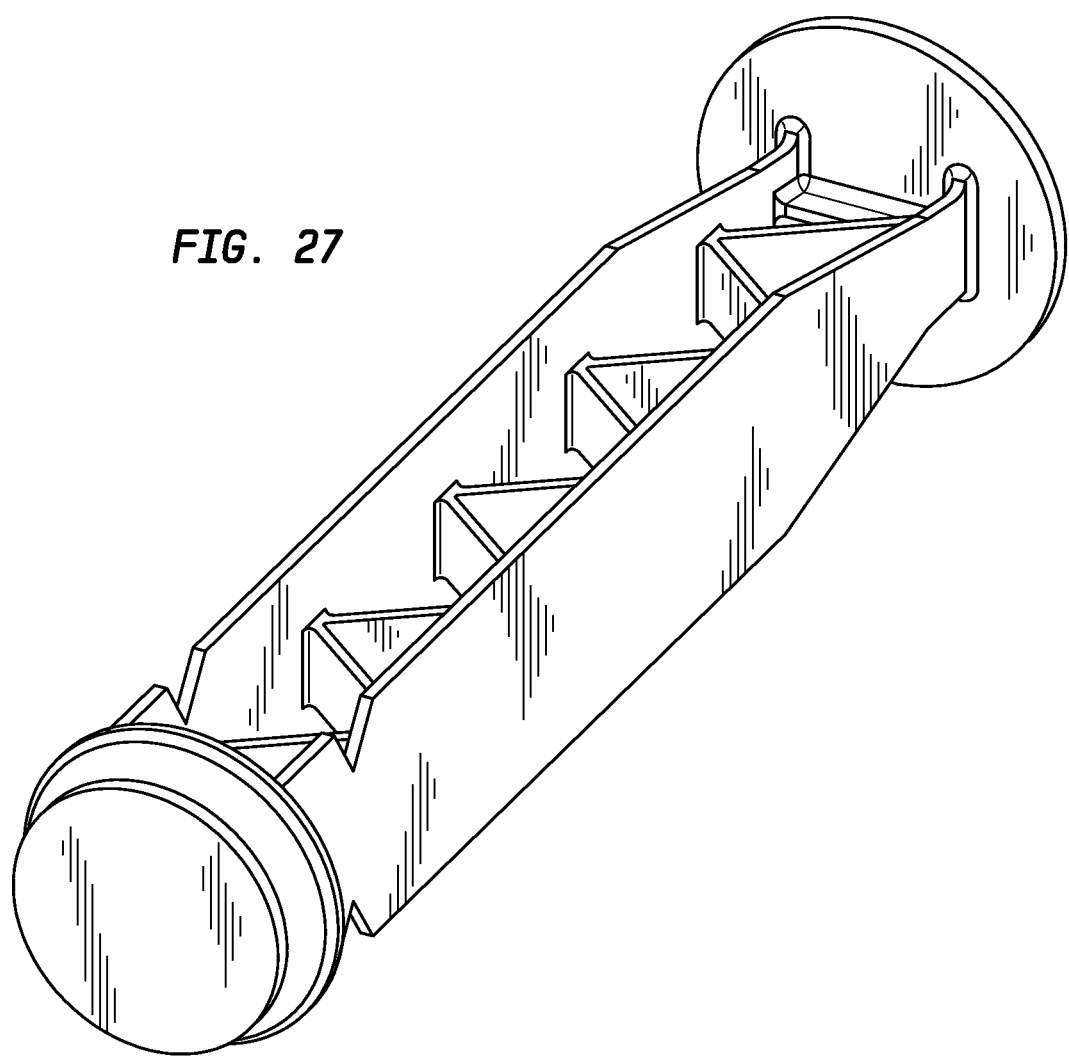
FIG. 27 illustrates a syringe plunger rod according to one or more embodiment of the invention.
Figure 28:
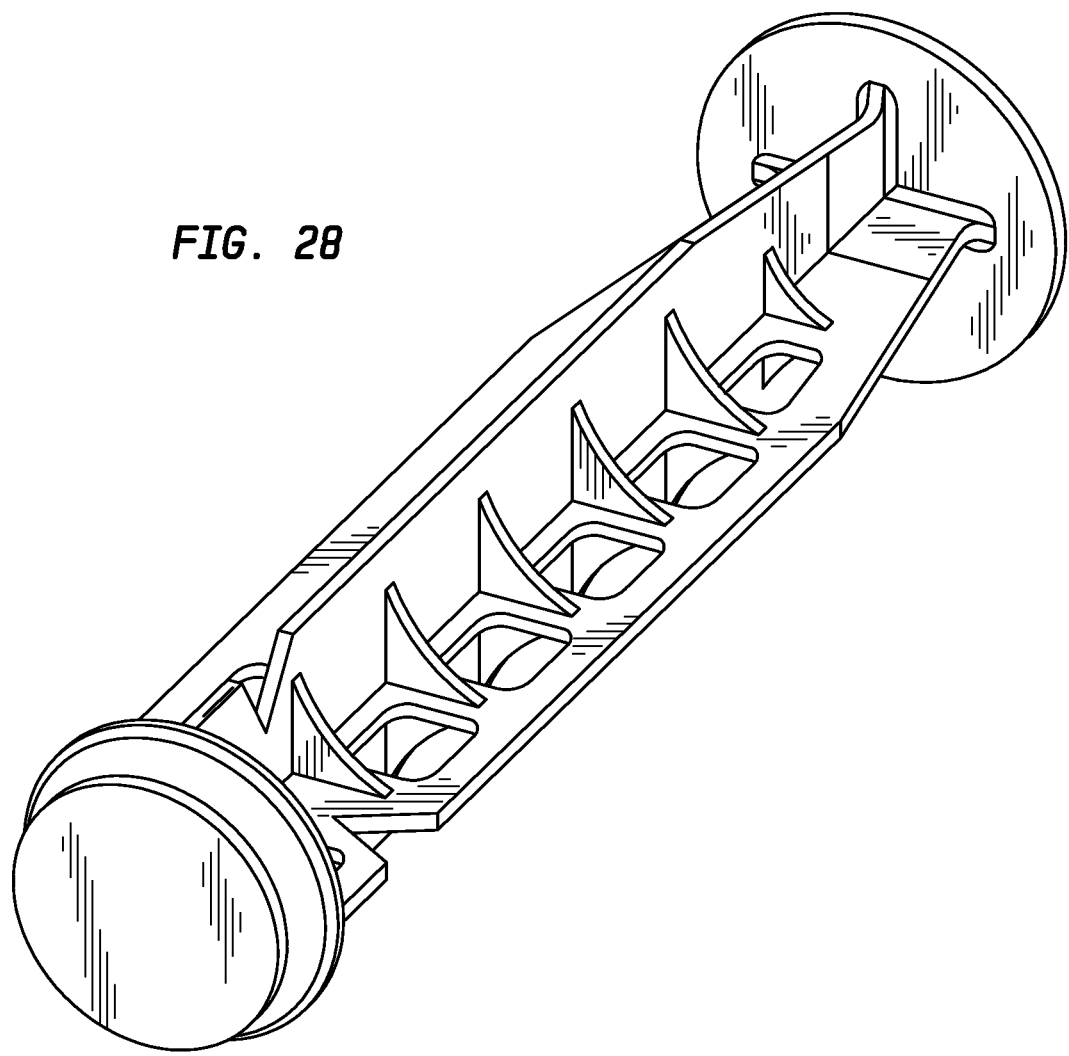
FIG. 28 illustrates a syringe plunger rod according to one or more embodiment of the invention.
Figure 29:
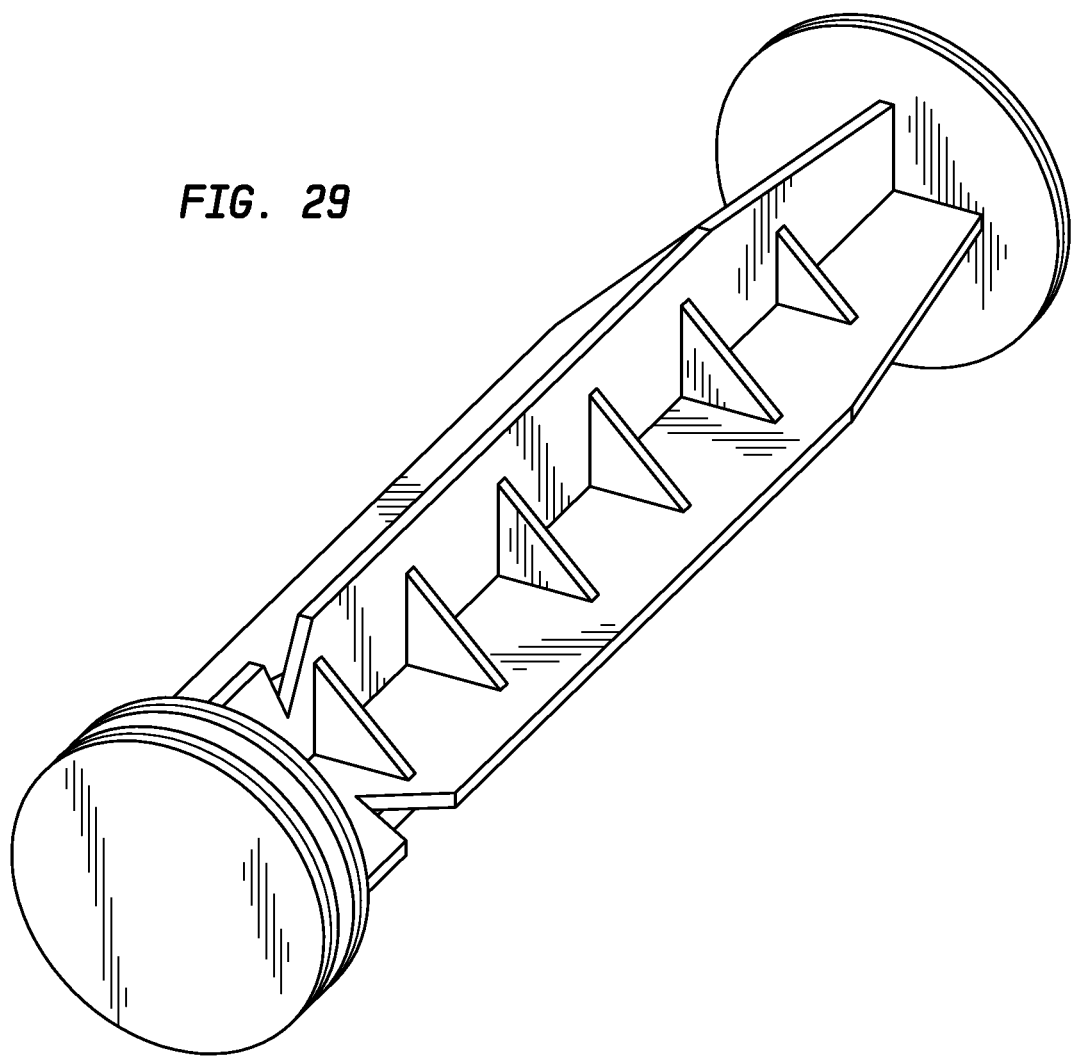
FIG. 29 illustrates a syringe plunger rod according to one or more embodiment of the invention.

FIG. 23A shows a detailed embodiment of the invention in which there are three main ribs extending the length of the elongate body. Referring to FIGS. 23A through 23F, a plurality of spaced openings extend along one of the three ribs. Additionally, there are a plurality of support walls adjacent the plurality of openings along the length of the elongate body. This provides a savings of material in the spaces and additional structural support with the support walls. FIG. 23B shows a top (or bottom) view of the plunger rod in FIG. 23A. FIG. 23C shows a left (or right) view of the plunger rod in FIG. 23A. FIGS. 23D and 23E show views looking down the thumbpress and down the stopper support, respectively. The cross-section shown in FIG. 23F illustrates the shape of the support walls.

Additional embodiments of the invention are directed to syringe plunger rods comprising an elongate body having at least one opening therethrough. The at least one opening can be along the length of the body so that the opening extends perpendicularly to the elongate axis, as shown in FIG. 5A. The at least one opening an extend along the length of the elongate body, as shown in FIG. 14A. In some embodiments, there are a combination of openings extending both along and perpendicular to the elongate axis. The syringe plunger rod can be make from a composition comprising one or more of virgin material, sterilization-stable recycled resin and a biobased composition.

In one or more embodiments, medical devices formed from the recycled resin compositions described herein do not change color after being sterilized which may be measured in terms of yellowness index. For example, the medical devices may be sterilized, as described above, and undergo no change in color or appearance.

The medical devices may be formed using various methods known in the art. For example, such methods include injection molding, blow molding, extrusion and/or roto or rotational molding. Other methods known in the art may also be utilized to form the medical devices or components.

The medical devices formed from the recycled resin composition described may include a plunger rod that exhibits functional performance acceptable to users and/or clinicians.

In one or more embodiments, a plunger rod formed from the recycled resin compositions described above exhibit the same functional performance as plunger rods formed from non-recycled resin compositions or compositions that do not include any recycled content.

A third aspect of the present invention pertains to a method for forming medical devices and components. In one or more embodiments, the method includes providing a melt blend composition of the recycled resin compositions described herein. The method includes stabilizing the melt blend composition and solidifying the composition in a pre-selected shape, which may include a plunger rod, a syringe barrel, a catheter, a blood collection device, a surgical blade handle, a needle shield and a needle hub. In one or more embodiments, stabilizing the melt blend composition includes stabilizing the melt blend composition to withstand exposure to gamma rays, electron beams, X-ray radiation and ethylene oxide gas without compromising functional performance and/or aesthetic appeal of the finished product.

According to one embodiment, the step of providing a melt blend composition comprises feeding a recycled resin component and one or more of an antioxidant component, a slip additive component, an anti-static component, an impact modifier component, a colorant component, an acid scavenger component, a melt blend component, a clarifier component, a X-ray fluorescence agent component, a radio-opaque filler component, a surface modifier component, a processing aid component and a reinforcing agent component into a melt compounding extruder. The step of solidifying the composition comprises one of injection molding the composition, extruding the composition and rotational molding the composition.

The recycled resin compositions, medical devices and components made from such compositions and the methods of making such medical devices and components provide a unique supply chain system which reduces the impact on landfills.

The present invention will be further understood by reference to the following non-limiting examples; however, the scope of the claims is not to be limited thereby.

EXAMPLES

The Inventive Formulations 1-6 were prepared by mechanically mixing recycled polypropylene resins with virgin polypropylene resins, wherein the virgin polypropylene resins further comprised of antioxidants, acid scavengers and melt-stabilizer.

Inventive Formulation 1 included 60% by weight of recycled polypropylene component A and 40% by weight of a virgin polypropylene component A. Virgin polypropylene component A included up to 0.8% by weight of an antioxidant component and a melt-stabilizer component and up to 0.3% by weight of an acid scavenger component.

Inventive Formulation 2 included 70% by weight of a recycled polypropylene component B and 30% by weight of virgin polypropylene component A, as described above.

Inventive Formulation 3 included 50% by weight of a recycled polypropylene component C and 50% by weight of a virgin polypropylene component A, as described above Inventive Formulation 4 included 60% by weight of recycled polypropylene component A and 40% by weight of a virgin polypropylene component B. Virgin polypropylene component B included up to 0.3% by weight of an antioxidant component and up to 0.2% by weight of an acid scavenger component.

Inventive Formulation 5 included 50% by weight of recycled polypropylene component B and 50% of virgin polypropylene component B, as described above.

Inventive Formulation 6 included 60% by weight of a recycled polypropylene component D and 40% by weight of virgin polypropylene component A, as described above.

The physical properties of each of Inventive Formulations 1-6 were analyzed. Specifically, the flexural modulus, tensile strength @ yield, tensile strength @ break, tensile elongation @ yield, tensile elongation @ break, tensile modulus, Izod impact strength and heat deflection temperature of Inventive Formulations 1-6 are evaluated and provided below in Table 1. For comparison, typical ranges for the physical properties of virgin polypropylene components are provided in Table 2.

The flexural modulus was measured according to ASTM D790-03. The tests were carried out on five specimens of each of the Inventive Formulations 1-6. The tests were carried out using a 0.05 in/min crosshead speed and a 2 inch support span length on an instrument provided by Instru-Met Corp., of Rahway, N.J., U.S.A. The specimens were formed using an injection molding process and conditioned at 23° C. and 50% relative humidity (RH) for 40 hours before the testing was performed. The average flexural modulus measurement of each of the five samples for Inventive Formulations is provided in Table 1.

The tensile properties of Inventive Formulations 1-6 were evaluated according to ASTM D638-03. The tests were carried out on five specimens of each of the Inventive Formulations 1-6. The tests were carried out using a crosshead speed of 2.0 in/min on an instrument provided by Instru-Met Corp., of Rahway, N.J., U.S.A. The type I tensile bar specimens were formed using an injection molding process and conditioned at 23° C. and 50% RH for 40 hours before the testing was performed. The average tensile strength @ yield, tensile strength @ break, tensile elongation @ yield, tensile elongation @ break and tensile modulus measurements of each of the five samples for Inventive Formulations is provided in Table 1.

The Izod impact strength of Inventive Formulations 1-6 were evaluated according to ASTM D256-02. The tests were carried out on ten specimens of each of the Inventive Formulations 1-6. The average Izod impact strength measurements for Inventive Formulations 1-6 are provided in Table 1.

The heat deflection temperature of Inventive Formulations 1-6 were evaluated according to ASTM D648-06 using an HDT/Vicat instrument available from Tinius Olsen, Inc. of Horsham, Pa., U.S.A. under a load of 66 psi. The average heat deflection temperature for Inventive Formulations 1-6 are provided in Table 1.

TABLE 1

Physical Properties of Inventive Formulations 1-6.

| | Inventive Formulation | | | | | |
|---|---|---|---|---|---|---|
| | 1 | 2 | 3 | 4 | 5 | 6 |
| Flexural Modulus (psi) | | | | | | |
| Average | 174345 | 148373 | 207247 | 187735 | 159857 | 157830 |
| Standard Deviation | 2153 | 1288 | 4749 | 4200 | 2629 | 1385 |
| Tensile Strength @ Yield (psi) | | | | | | |
| Average | 4694 | 4372 | 4959 | 4919 | 4737 | 4408 |
| Standard Deviation | 77 | 74 | 100 | 42 | 41 | 56 |
| Tensile Strength @ Break (psi) | | | | | | |
| Average | 2228 | 2665 | 4044 | 4058 | 2740 | 2798 |
| Standard Deviation | 304 | 81 | 779 | 162 | 81 | 84 |
| Tensile Elongation @ Yield (%) | | | | | | |
| Average | 9.67 | 11.1 | 8.37 | 7.87 | 9.27 | 8.41 |
| Standard Deviation | 0.750 | 0.558 | 0.255 | 0.515 | 0.436 | 0.939 |
| Tensile Elongation @ Break (% i) | | | | | | |

TABLE 1-continued

Physical Properties of Inventive Formulations 1-6.

| | Inventive Formulation | | | | | |
|---|---|---|---|---|---|---|
| | 1 | 2 | 3 | 4 | 5 | 6 |
| Average | 116 | 254 | 24.8 | 23.2 | 165 | 241 |
| Standard Deviation | 141 | 121 | 15.3 | 3.50 | 40.5 | 62.3 |
| Tensile Modulus (psi) | | | | | | |
| Average | 238539 | 205376 | 264521 | 251694 | 234553 | 234458 |
| Standard Deviation | 7031 | 11233 | 6799 | 9940 | 11561 | 2841 |
| Izod Impact Strength (ft-lbs/in) | | | | | | |
| Average | 0.46 | 0.51 | 0.53 | 0.53 | 0.44 | 0.51 |
| Heat Deflection Temperature (° C.) | | | | | | |
| Average | 84.6 | 77.8 | 109.3 | 92.2 | 96.1 | 104.9 |

TABLE 2

Typical Physical properties of Virgin polyolefin resins.
Physical Properties

| | |
|---|---|
| Flexural Modulus | 145037.7 psi (1000 MPa)-290075.4 psi (2000 MPa) |
| Tensile strength @yield | 3625.9 psi (25 MPa)-6526.7 psi (45 MPa) |
| Tensile elongation @yield | 6%-15% |
| Tensile Modulus | 145037.7 psi (1000 MPa)-261067.9 psi (1800 MPa) |
| Notched Izod Impact Strength | 0.3 ft-lb/in-1.0 ft-lb/in |
| Heat Deflection Temperature | 70° C.-110° C. |

The physical properties of the Inventive Formulations 1-6 are comparable to the physical properties of virgin polyolefin resins, shown in Table 2. Accordingly, the recycled resin compositions described herein achieve the goals of utilizing recycled resins that are biocompatible and useful for medical device applications, without compromising the physical properties of the resulting devices.

Inventive Formulations 1-6 were also analyzed for biocompatibility. Specifically, each of Inventive Formulations 1-6 was analyzed in accordance with ANSI/AAMI/ISO 10-993-5 and the United States Pharmacopeia Biological Tests and Assays, Biological Reactivity Tests, in Vitro <87>. The United States Pharmacopeia Biological Reactivity Tests, in Vitro <87> are designed to determine the biological reactivity of mammalian cell cultures following contact with elastomeric plastics and other polymeric materials with direct or indirect patient contact or of specific extracts prepared from the materials under test. The elution test described in United States Pharmacopeia Biological Reactivity Tests, in Vitro <87> was carried out on Inventive Formulations 1-6.

Each of Inventive Formulations 1-6 passed or met the standard for the cytotoxicity tests with a United States Pharmacopeia score of zero, thereby meeting the criteria for preclinical toxicological safety evaluation established by United States Pharmacopeia and ISO 10-993-5. All of the biocompatibility tests were conducted in accordance with Good Laboratory Practice or GLP principles following procedures known in the art.

Reference throughout this specification to "one embodiment," "certain embodiments," "one or more embodiments" or "an embodiment" means that a particular feature, structure, material, or characteristic described in connection with the embodiment is included in at least one embodiment of the invention. Thus, the appearances of the phrases such as "in one or more embodiments," "in certain embodiments," "in one embodiment" or "in an embodiment" in various places throughout this specification are not necessarily referring to the same embodiment of the invention. Furthermore, the particular features, structures, materials, or characteristics may be combined in any suitable manner in one or more embodiments.

Although the invention herein has been described with reference to particular embodiments, it is to be understood that these embodiments are merely illustrative of the principles and applications of the present invention. It will be apparent to those skilled in the art that various modifications and variations can be made to the method and apparatus of the present invention without departing from the spirit and scope of the invention. Thus, it is intended that the present invention include modifications and variations that are within the scope of the appended claims and their equivalents.

What is claimed is:

1. A syringe plunger rod comprising:
    an elongate body having a proximal end and a distal end defining a length and consisting of three ribs extending the length of the body, at least one of the three ribs having a plurality of spaced openings spaced along the length, and a plurality of support walls contacting two of the three ribs, the support walls spaced along the length of the elongate body and dispersed in one or more of the openings;
    a thumbpress positioned at the proximal end of the elongate body; and
    a stopper support positioned at the distal end of the elongate body,
    wherein each of the elongate body and stopper support comprise compositions comprising a mixture of 50% to 70% by weight of a recycled resin and 30% to 50% by weight of a virgin resin, wherein the recycled resin is selected from a combination of post-industrial recycled resin and post-consumer recycled resin, wherein the compositions pass or meet a United States Pharmacopeia score of zero for cytotoxicity;
    wherein the recycled resin is a recycled polypropylene and the virgin resin is a virgin polypropylene;

wherein the plurality of spaced openings occur at an intersection of at least two of the ribs, wherein the spaced openings have a spherical shape with its center at the intersection;

wherein the syringe plunger rod is a fluid path contact medical device.

2. The syringe plunger rod of claim 1, wherein the composition further comprises one or more of an antioxidant component, slip additive component, anti-static component, impact modifier component, colorant component, acid scavenger component, x-ray fluorescence agent component, radio-opaque filler component, surface modifier component, processing aid component, melt stabilizer, clarifiers or reinforcing agent component.

* * * * *

UNITED STATES PATENT AND TRADEMARK OFFICE
CERTIFICATE OF CORRECTION

PATENT NO. : 11,324,861 B2
APPLICATION NO. : 14/868289
DATED : May 10, 2022
INVENTOR(S) : Ankur S. Kulshrestha et al.

It is certified that error appears in the above-identified patent and that said Letters Patent is hereby corrected as shown below:

In the Specification

Column 7, Line 29, after "include" replace "buylated" with "butylated".

Signed and Sealed this
Twenty-eighth Day of June, 2022

Katherine Kelly Vidal
*Director of the United States Patent and Trademark Office*